| United States Patent [19]
Rollin et al.

[11] Patent Number: 5,853,980
[45] Date of Patent: Dec. 29, 1998

[54] BLACK CREEK CANAL HANTAVIRUS AND RELATED METHODS

[75] Inventors: Pierre E. Rollin, Lilburn; Luanne Elliott, Atlanta; Thomas G. Ksiazek, Lilburn; Stuart T. Nichol, Atlanta; Sergey Morzunov, Atlanta; Eugeny Ravkov, Atlanta, all of Ga.

[73] Assignees: The United States of America as represented by the Department of Health and Human Services, Washington, D.C.; National Institutes of Health Office of Technology Transfer, Bethesda, Md.

[21] Appl. No.: 792,055

[22] Filed: Feb. 3, 1997

Related U.S. Application Data

[63] Continuation of Ser. No. 390,361, Feb. 17, 1995, abandoned.

[51] Int. Cl.$^6$ .............................. C12Q 1/70; C12Q 1/68; A61K 39/12; C07H 21/04

[52] U.S. Cl. .................................. 435/5; 435/6; 435/69.1; 435/69.3; 435/172.3; 435/235.1; 435/252.3; 435/320.1; 424/204.1; 424/93.2; 530/350; 530/389.4; 530/387.1; 536/23.72; 536/24.32; 935/65

[58] Field of Search ................................ 424/204.1, 93.2; 435/235.1, 320.1, 69.1, 69.3, 172.3, 5, 6, 252.3; 935/65; 536/23.72, 24.32; 530/350, 389.4, 387.1

[56] References Cited

PUBLICATIONS

Mills et al. "Rodents and hantavirus:New Findings from the Americas and their Disease Implications". Hantavirus Infections in the United States symposium; American Society of Microbiology. vol. 34, p. 284, 1994.

Khan et al."Fatal Hantavirus Pulmonary Syndrome in an adolescent". Pediatrics, vol. 95, No. 2, pp. 276–280, Feb. 2, 1995.

Hjelle et al. "Progress in the Development of Hantavirus Diagnosis assays–United States". JAMA, vol. 270, No. 16, pp. 1920–1921, Oct. 27, 1993.

Plyusnin et al., "Sequences of wild–Puumala virus genes show a correlation of genetic variation with geographic origin of the strains," *Journal of General Virology* 75:405–409 (1994).

Elliott et al., "Isolation of the Causative Agent of Hantavirus Pulmonary Syndrome," *Am. J. Trop. Med. Hyg.* 51(1):102–108 (1994).

Anapol et al., "Newly–Identified Hantavirus—Florida, 1994," *Morbidity and Mortality Weekly Report* 43(6):99, 105 (1994).

Jenison et al., "Characterization of Human Antibody Responses to Four Corners Hantavirus Infections among Patients with Hantavirus Pulmonary Syndrome," *Journal of Virology* 68(5):3000–3006 (May, 1994).

Duchin et al., "Hantavirus Pulmonary Syndrome: A Clinical Description of 17 Patients with a Newly Recognized Disease," *New England Journal of Medicine* 330:949–955 (Apr. 7, 1994).

Spiropoulou et al., "Genome Structure and Variability of a Virus Causing Hantavirus Pulmonary Syndrome," *Virology* 200:001–009 (1994).

Childs et al., "Serologic and Genetic Identification of *Peromyscus maniculatus* as the Primary Rodent Reservoir for a New Hantavirus in the Southwestern United States," *The Journal of Infectious Diseases* 169:1271–1280 (1994).

Chu et al., "Serological Relationships among Viruses in the Hantavirus Genus, Family Bunyaviridae," *Virology* 198:196–204 (1994).

Xiao et al., "Nucleotide and deduced amino acid sequences of the M and S genome segments of two Puumala virus isolates from Russia," *Virus Research* 30:97–105 (1993).

Xiao et al., "Molecular and antigenic characterization of HV114, a hantavirus isolated from a patient with haemorrhagic fever with renal syndrome in China," *Journal of General Virology* 74:1657–1659 (1993).

Feldmann et al., "Utilization of autopsy RNA for the synthesis of the nucleocapsid antigen of a newly recognized virus associated with hantavirus pulmonary syndrome," *Virus Research* 30:351–367 (1993).

Nichol et al., "Genetic Identification of a Hantavirus Associated with an Outbreak of Acute Respiratory Illness," *Science* 262:914–917 (Nov. 5, 1993).

Vapalahti et al., "Cloning and sequencing of Puumala virus Sotkamo strain S and M RNA segments: evidence for strain variation in hantavirus and expression of the nucleocapsid protein," *Journal of General Virology* 73:829–838 (1992).

Parrington et al. "Molecular characterization of the Propect Hill virus M RNA segment: a comparison with the M RNA segments of other hantavirues," *Journal of General Virology* 72:1845–1854 (1991).

Parrington and Kang, "Nucleotide Sequence Analysis of the S Genomic Segment of Prospect Hill Virus: Comparison with the Prototype Hantavirus," *Virology* 175:167–175 (1990).

*Primary Examiner*—Marian C. Knode
*Assistant Examiner*—Datquan Lee
*Attorney, Agent, or Firm*—Fitch, Even, Tabin & Flannery

[57] ABSTRACT

The present invention relates to the discovery and isolation of a novel hantavirus designated the Black Creek Canal hantavirus. In particular, the present invention relates to nucleic acids of the newly discovered virus and to nucleic acid reagents (primers and probes), purified polypeptides and antibodies for use in methods of detection and prevention of infection by the virus. A vaccine or purified immunogenic polypeptide of the Black Creek Canal hantavirus in a pharmaceutically acceptable carrier is provided. A vector comprising the nucleic acids of the invention is provided. A method of detecting the presence of a hantavirus in a subject comprising contacting an antibody-containing sample from the subject with a purified polypeptide of the invention and detecting the reaction of the polypeptide and the antibody is provided. A method of detecting the presence of the Black Creek Canal hantavirus is provided comprising reverse transcribing viral RNA to synthesize a complementary DNA sequence followed by amplifying the DNA using primers which are selective for the Black Creek Canal hantavirus and detecting the presence of amplification, thereby indicating presence of the Black Creek Canal hantavirus in the sample.

4 Claims, 1 Drawing Sheet

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 1989 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

| | | | | | |
|---|---|---|---|---|---|
| TAGTAGTAGA | CTCCTTGAGA | AGCTACTACT | AAAGAAGCTG | TAATGAGCAA | CCTCAAAGAA | 60 |
| GTTCAGGACA | ATATTACAAC | CCACGAACAG | CAGCTAGTGG | CAGCTAGACA | AAAGCTGAAA | 120 |
| GATGCAGAAA | GGACGGTTGA | GGTGGACCCG | GATGACGTTA | ACAAGAGCAC | ACTACAGAAC | 180 |
| AGACGGGCAG | CTGTGTCTGC | ATTGGAGGCC | AAAATTGGGG | AGCTCAAGAG | ACAACTTGCA | 240 |
| GATCTTGTTG | CAGCTCAGAA | ATTGGCTACA | AAATCTGTTG | ATCCAACAGG | GATTGAACCT | 300 |
| GATGACCATC | TGAAAGAAAA | GTCCTCACTT | AGGTATGGCA | ATGTGCTTGA | CGTCAATTCA | 360 |
| ATTGACCTTG | AGGAACCAAG | TGGGCAGACT | GCTGACTGGA | AAGCAATCGG | GACTTATATT | 420 |
| CTTAGTTTTG | TCCTTCCAAT | TGTGTTGAAG | GCCCTCTATA | TGTTGTCAAC | ACGAGGAAGG | 480 |
| CAGACAGTTA | AGGAAAATAA | AGGGACAAGA | ATCAGATTCA | AGGATGATTC | TTCTTATGAA | 540 |
| GATGTTAATG | GTATTCGGAA | GCCCAAACAC | TTGTATGTGT | CCTTGCCTAC | AGCACAGTCA | 600 |
| ACAATGAAGG | CAGATGAGAT | CACACCAGGT | CGATTCCGTA | CTATTGTATG | TGGGTTATTC | 660 |
| CCTGCACAGA | TTAAAGCACG | GAATATTATA | AGCCCTGTCA | TGGGAGTGAT | TGGGTTTTCA | 720 |
| TTCTTTGTGA | AGGATTGGGT | TGATAAAATT | GAGGACTTTT | TAAGGGCTGA | ATGTCCATTC | 780 |
| CTACCAAAAC | CAAGGGCACA | AGCAGAGTCA | TTCCTGTCGA | CAAATGGTGC | TTACTTTATG | 840 |
| AATAGACAGA | CACAGGTTGA | AGAGTCAAAG | GTGCAGGACA | TTTTAGACCT | AATTGACACT | 900 |
| GCTGAATCAG | GGGGTGCAAC | ATTATTTGAT | AATATTGCTA | GCCCTCAATC | TGCATGGATA | 960 |
| TTTGCCTGTG | CACCGGACCG | ATGTCCACCG | ACAGCATTGT | ATGTTGCTGG | TGTGCCTGAA | 1020 |
| TTAGGAGCAT | TCTTTTCAAT | ACTCCAAGAT | ATGAGGAATA | CAATTATGGC | ATCTAAGTCT | 1080 |
| GTAGGAACTG | CTGAAGAAAA | ACTGAAAAAG | AAATCTGCCT | TCTACCAGTC | TTACTTACGC | 1140 |
| AGAACACAGT | CAATGGGGAT | TCAACTGGAC | CAGAAAATCA | TTATATTGTA | TATGATTAAC | 1200 |
| TGGGGAAAAG | AGGCTGTCAA | CCACTTTCAT | CTCGGGGATG | ACATGGATCC | TGAATTGCGG | 1260 |
| CAGCTAGCAC | AAGCCTTAGT | AGACACTAAG | GTTAAAGAGA | TTTCAAATCA | AGAGCCTTTA | 1320 |
| AAGATATGAG | TGCTTAATCT | AACATGGAGT | GGCTCTGTTA | TAACTGAATG | TTATTTCGGG | 1380 |
| TTGGTGCCAA | TTATTAATCA | TCTCAGGTTC | TTTCCTTTAA | ATTACGGGTG | GGTTAGATAG | 1440 |
| AGAATGTATA | ATCCTTTACT | GTGACGGGTG | GTTCAATAGG | GCATTTATGG | GTCATATTAT | 1500 |
| TTAGTTATAA | TTAGATTAAG | ATTAGGATTA | AGGTTAAGAT | TAAACTTTAG | GTTAAGGTTA | 1560 |
| TAATTGCTAG | TATGTTAATG | ATAAGTTAGA | TTAGACATAA | CTATAGTTTA | AAATAGCTCA | 1620 |
| AGTAGTATTA | GTATAATTAG | TATAGTTATT | AAATGGTAAT | TTAGTCTATA | GACCTAGTTA | 1680 |
| ATGATTGAAA | TCTATATAGT | TAGTTTGTGT | TAAATAGGTT | GTAGTTATGT | TTAGTTAATG | 1740 |
| TTAGAATTAT | ACATACTATT | AATGTGATTT | ATACTGTCGG | ATACACTGGA | GCTACTATAG | 1800 |
| TAGAACTTGC | TTTACTAACT | ACTGATCCTT | ACAAATTGAT | GTAAATTTCA | TTGTATGCTT | 1860 |
| AAGCTTTAGC | TACTAATTAT | ATACTAACAA | CAACATCTAC | CTCATCCTAA | ACCCTCAACC | 1920 |
| CTAACCTACC | TCTTACATTC | TACCTCAGAG | TTTATGTTTC | TTGATTGCTT | TTCAAGGAGC | 1980 |
| ATACTACTA | | | | | | 1989 |

( 2 ) INFORMATION FOR SEQ ID NO:2:

( i ) SEQUENCE CHARACTERISTICS:
        ( A ) LENGTH: 3668 base pairs
        ( B ) TYPE: nucleic acid
        ( C ) STRANDEDNESS: double ( D ) TOPOLOGY: linear ( i i ) MOLECULE TYPE: DNA (genomic)

( x i ) SEQUENCE DESCRIPTION: SEQ ID NO:2:

| | | | | | |
|---|---|---|---|---|---|
| TAGTAGTAGA | CTCCGCAAGA | AGAAGCAAGA | CAAAAAAGA | CTGAGAGCAA | TATGGGCAGG | 60 |
| TTATACCTGA | TTGTGCTTGG | GGTCCTGATT | ACTGCTACAG | CTGGTTTCCC | GCGGAGTGTG | 120 |
| CATGAATTAA | AAATTGAATG | CCCGCATACT | GTCGTATTAG | GGCAAGGATA | TGTCACAGGT | 180 |
| TCTGTTGAGC | TTGGCTTTAT | TGCTCTTGAT | CAAGTAACAG | ATTTAAAGAT | TGAGAGCTCC | 240 |
| TGTAGCTTTG | ATCATCATGC | AGCACCTACA | ACAACACAGA | ACTTCACACA | GCTCAAATGG | 300 |
| GCAAAAACAG | CAAGCACAAC | TGACACCACA | AATGCAGCCG | AGACTACATT | TGAAAGCAAG | 360 |
| TCCACGGAAG | TGCACTTAAA | AGGAGTATGT | ACAATTCCCA | GCAATGTGCT | CGACGGACCA | 420 |
| TCTCGCCCTG | TAACAGGGAG | AAAAACAGTT | GTCTGTTATG | ATTTAGCATG | CAATCAAACT | 480 |
| CATTGTCAGC | CAACTGTTCA | TTTGCTAGCA | CCAATACAAA | CATGCATGTC | TGTTCGGAGC | 540 |
| TGTATGATAA | GCTTATTGGC | AAGTAGGATT | CAGGTGGTCT | ATGAGAAGAC | ATACTGTGTT | 600 |
| ACAGGACAAC | TTATAGAAGG | CTTGTGTTTT | AACCCTGTCC | CTAACCTTGC | ACTGACACAA | 660 |
| CCTGGGCACA | CATATGACAC | ATTTACATTG | CCAATTACAT | GCTTTCTGGT | GGCCAAAAAG | 720 |
| GGTGCAAACC | TGAAAATTGC | TGTTGAGCTA | GAGAAACTGA | CAACAAAGAC | TGGTTGTGCA | 780 |
| GAAAATGCAC | TTCAGGCTTA | CTATATATGC | TTTATAGGAC | AGCACTCTGA | GCCATTAACT | 840 |
| GTCCCGATGC | TCGAGGACTA | TAGATCAGCT | GAAATTTTCA | CAAGAATAAT | GATGAATCCA | 900 |
| AAAGGTGAAG | ATCATGATAT | GGAACAGTCT | TCCCAAGGTG | CTTTGCGAAT | TGTTGGGCCT | 960 |
| ATAAAGGTA | AAGTGCCACC | CACTGAGACA | TCAGACACTG | TGCAGGGGAT | TGCTTTTGCA | 1020 |
| GGTTTGCCTA | TGTATAGTTC | TTTTTCGAGC | CTTGTAAGGA | AAGCAGAACC | TGAATATCTA | 1080 |
| TTTTCACCTG | GTATCATTGC | AGAATCTAAT | CATAGCAGCT | GCGATAAGAA | AACATTACCC | 1140 |
| TTAACATGGA | GGGGTTTCTT | ATCAATGTCT | GGTGAAATTG | AAAGAATTAC | TGGCTGTAAT | 1200 |
| GTCTTTTGTA | CACTTGCTGG | CCCAGGTGCA | AGTTGTGAGG | CTTACTCTGA | AAATGGAATA | 1260 |
| TTCAATATTA | GTTCTCCCAC | ATGCTTAGTC | AATAAAGTCC | AAAAGTTTAG | GGGCTCAGAA | 1320 |
| CAGAGAATCA | ACTTTATCTC | CCAAAGAATA | GATCAAGATG | TGATTGTCTA | TTGTAATGGA | 1380 |
| CAAAAGAAGG | TCATTCTGAC | AAAAACACTA | GTTATAGGCC | AATGTATTTA | TACATTTACA | 1440 |
| AGTATCTTTT | CACTGATCCC | TAGTGTTGCA | CATTCCTTGG | CTGTCGAGCT | CTGTGTACCA | 1500 |
| GGGATCCATG | GATGGGCTAC | AATTGCATTA | GTAATCACAT | TTTGCTTTGG | CTGGTTACTT | 1560 |
| ATTCCTACCA | CAACCATGGT | TGTGTTGAAA | TGCCTGAGGC | TGCTAACTTA | CTCGTGCTCT | 1620 |
| CACTATTCTA | CTGAATCAAA | GTTCAAAGTC | ATTCTAGAAA | AGGTGAAGGT | TGAATACCAG | 1680 |
| AAGACAATGG | GTTCAATGGT | ATGTGACATT | TGTCATCATG | AATGTGAAAC | AGCAAAGAA | 1740 |
| CTTGAAAGCC | ATAAAAAAAG | TTGTGCTGAT | GGGCAGTGCC | CATACTGTAT | GACTATTACC | 1800 |
| GAGGCAACTG | AGAGTGCTTT | ACAGGCCCAT | TATGCTGTAT | GTAAATTAAC | AGGGCGCTTT | 1860 |
| CATGAGGCTT | TAAAAAAATC | ATTAAAAAAA | CCAGAGGTTC | AGAGGGGTTG | TTATAGAACA | 1920 |
| CTTGGTGTTT | TCCGTTATAA | GAGTCGTTGC | TATGTGGGCT | TAGTATGGAT | GTGTTTGTTG | 1980 |
| ACTCTTGAGT | TGATCGTTTG | GGCTGCTAGT | GCAGATACAC | CCTTACTTGA | ACCTGGCTGG | 2040 |
| TCAGATACAG | CTCATGGGGT | AGGTGATATT | CCGATGAAGA | CAGACCTAGA | GTTAGATTTT | 2100 |
| GCTATCCCAT | CATCTTCATC | ATATAGTTAT | AGAAGGCGAT | TAGTAAACCC | TGCTAATTCA | 2160 |
| GATGAGACTG | TTCCATTTCA | CTTTCAGCTT | GAACGACAAG | TAATCCATGC | AGAAATACAA | 2220 |

| | | | | | | |
|---|---|---|---|---|---|---|
| TCGCTAGGAC | ATTGGATGGA | TGCCACATTT | AATATAATTT | CTGCATTTCA | CTGCTATGGT | 2280 |
| GAGTGCAAGA | AATACTCTTA | CCCTTGGCAA | ACAGCAAAAT | GTTTTTTTGA | GAAGGACTAC | 2340 |
| CAGTATGAAA | CAAGTTGGAG | CTGTAATCCG | CCAGACTGTC | CAGGGGTAGG | TACTGGTTGT | 2400 |
| ACTGCATGTG | GCATATATCT | GGATAAATTG | AAGTCTGTTG | GGAAAGCATA | TAAAGTAATT | 2460 |
| ACCTTGAAAT | ATGCAAGAAA | AGTTTGCATT | CAATTAGGTA | CGGAACAAAC | ATGTAAGAAT | 2520 |
| ATCGATGTTA | ATGACTGTCT | TGTAACTTCA | TCAATCAAAG | TTTGTATGAT | TGGCACAATC | 2580 |
| TCAAAGTTTC | AACCAGGAGA | CACTTACTA | TTTTGGGTC | CACTTGAAGA | AGGTGGCCTA | 2640 |
| GTCCTCAAAC | AATGGTGTAC | AACAACATGT | TCATTGGTG | ATCCAGGTGA | TATTATGTCT | 2700 |
| ACAACTTCAG | GAATGCGTTG | CCCTGAACAT | ACAGGCTCCT | TTAGGAAGAT | CTGTGGGTTT | 2760 |
| GCAACAACAC | CTGTTTGTGA | GTATCAAGGG | AATACAGTCT | CTGGTTTTAA | AAGATTGATG | 2820 |
| GCTACAAAGG | ACTCGTTTCA | GTCATTTAAT | GTATCTGAAG | TACACATTAC | AACAACCAAG | 2880 |
| CTAGAATGGA | GTGATCCTGA | TAGTAACATC | AAAGATCATA | TAAATTTGAT | TTTAAACCGA | 2940 |
| GATGTATCAT | TTCAAGACTT | AAGTGACAAT | CCGTGCAAAG | TGGACCTTTC | AACACAGGCA | 3000 |
| ATTGATGGTG | CATGGGCTC | TGGTGTAGGT | TTTACATTGA | CATGTATAGT | GGGATTAACA | 3060 |
| GAATGCTCTA | GTTTCATGAC | CTCTATTAAG | GTATGTGACA | TGGCTATGTG | TTATGGAGCC | 3120 |
| TCAGTAGTAA | ACCTAGTTAG | AGGCTCCAAT | ACAGTTAAAA | TTGTTGGAAA | AGGTGGTCAT | 3180 |
| TCTGGTTCGA | CATTTAGATG | CTGTCATGAT | AAGGACTGTA | CAAGTAATGG | TCTGCTTGCA | 3240 |
| TCTGCACCAC | ATCTTGAACG | GGTTACAGGA | TTCAATCAGA | TAGATTCTGA | CAAGGTTTAT | 3300 |
| GATGATGGAG | CTCCACCGTG | TTCTATAAAA | TGCTGGTTTG | CAAAGTCAGG | TGAGTGGCTT | 3360 |
| TTGGGGATAT | TAAATGGAAA | TTGGGTAGTT | GTTGCAGTCC | TTGTTATCAT | ATTACTAATC | 3420 |
| TCTATCTTTC | TATTCAGCTT | CTTCTGCCCC | ATAAGATCTC | ACAAAAGCA | ACTTTAAATA | 3480 |
| GCCTCTAACC | ACCCTTAATA | ACAATGACTA | TAAAGCACTA | ACAATTGCT | AAAATATTGC | 3540 |
| CAAGATAACA | GCTAACCACT | TTAATCTGTA | TGACAATGAA | TAACATCACT | AAAAAAAACT | 3600 |
| AAGAATTTAA | TAACATATAA | TAGATTTGCC | TCAAACCAGG | GCTTTTGTTC | CTGCGGAGCA | 3660 |
| TACTACTA | | | | | | 3668 |

( 2 ) INFORMATION FOR SEQ ID NO:3:

( i ) SEQUENCE CHARACTERISTICS:
        ( A ) LENGTH: 410 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

| | | | | | | |
|---|---|---|---|---|---|---|
| AAATAATAAA | GTGAGGTTTT | ATTCTAAAGT | AAGACAACAT | GGTTTAACGG | TTGATCAATC | 60 |
| TACTGTGGGT | GCAAGTGGTG | TTTATCCGTC | CTTAATGTCC | CGGGTAGTCT | ACAAACATTA | 120 |
| CAGGAGCTTA | ATTTCAGAGG | CAACTACCTG | TTTCTTTCTA | TTCGAAAAAG | GGTTACACGG | 180 |
| CAATCTGACA | GAGGAGGCTA | AAATTCACTT | AGAAACTGTA | GAATGGGCTA | GAAAGTTCAA | 240 |
| TGAGAAAGAG | AATAGATATG | GTGATATTTT | GATGAAAGAA | GGGTATACAA | TTGAGTTAGT | 300 |
| TGAAAATCCA | AATGTGACCG | TAGAACAGCA | ATTATTCTGT | CAAGAGGTTG | TTGAGCTCAG | 360 |
| TGCAATGGAG | CTAAATAAAT | ACTTACATGC | CAAATCTCAA | GTTACTGTGT | | 410 |

( 2 ) INFORMATION FOR SEQ ID NO:4:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (ii) MOLECULE TYPE: Oligonucleotide (xi) SEQUENCE DESCRIPTION: SEQ ID NO:4:

CTCCTTGAAA AGCTACTACG ACTAAAGCTG GAATGA                36

(2) INFORMATION FOR SEQ ID NO:5:

(i) SEQUENCE CHARACTERISTICS:
    (A) LENGTH: 34 base pairs
    (B) TYPE: nucleic acid
    (C) STRANDEDNESS: single
    (D) TOPOLOGY: linear (ii) MOLECULE TYPE: Oligonucleotide (xi) SEQUENCE DESCRIPTION: SEQ ID NO:5:

CAGGTCGACA TTATATCTTT AGTGGTTCTT GGTT                  34

(2) INFORMATION FOR SEQ ID NO:6:

(i) SEQUENCE CHARACTERISTICS:
    (A) LENGTH: 42 base pairs
    (B) TYPE: nucleic acid
    (C) STRANDEDNESS: single
    (D) TOPOLOGY: linear (ii) MOLECULE TYPE: Oligonucleotide (xi) SEQUENCE DESCRIPTION: SEQ ID NO:6:

CAGCTGCAGG GAATGAGCAC CCTCAAAGAA GTGCAAGACA AC         42

(2) INFORMATION FOR SEQ ID NO:7:

(i) SEQUENCE CHARACTERISTICS:
    (A) LENGTH: 45 base pairs
    (B) TYPE: nucleic acid
    (C) STRANDEDNESS: single
    (D) TOPOLOGY: linear (ii) MOLECULE TYPE: Oligonucleotide (xi) SEQUENCE DESCRIPTION: SEQ ID NO:7:

CAGCTGCAGA TTATATCTTT AGTGGTTCTT GGTTAGAGAT TTCCC      45

BLACK CREEK CANAL HANTAVIRUS AND RELATED METHODS

This application is a continuation of application Ser. No. 08/390,361, filed Feb. 17, 1995, now abandoned.

BACKGROUND OF THE INVENTION

1. Field of the Invention

The present invention relates to discovery of a new hantavirus species. In particular, the present invention relates to the isolated Black Creek Canal hantavirus, to attenuated or inactivated derivatives of the Black Creek Canal hantavirus, to nucleic acids of the new hantavirus, and to nucleic acid reagents and antibodies for use in methods of detection and prevention of infection by the new virus.

2. Background Art

In general, hantaviruses are spherical 28-nm viruses that were initially identified from the feces of rodents. They have distinctive ultrastructural glycoprotein surfaces of 5–10 nm that are embedded in a lipid bi-layer envelope. The negative sense RNA of the viral genome consists of three segments, generally designated as S, M, and L for the small, medium, and large genome fragments, respectively. The S segment encodes a nucleocapsid protein (N) and the M segment encodes the surface glycoproteins G1 and G2. (Schmaljohn, C. S. et al., Fund. Virol. 545:545 (1991)). The S segment may additionally encode a $6 \times 10^3$-dalton protein. (Bishop, D. H. L. Bunyaviridae and their replication. In, Virology, 2nd ed. B. N. Fields and D. M. Knipe, Eds. Raven Press, Ltd. (1990)). The L segment encodes the viral polymerase gene. (Elliott, M. Molecular biology of the Bunyaviridae. J. Gen. Virol. 71:501–522 (1990)). Seven species of hantavirus are currently recognized and are designated Hantaan (HTN) virus species, Seoul (SEO) virus species, Puumala (PUU) virus species, Dobrava-Belgrade (DOB) virus species, Prospect Hill virus species (PH), Harvest Mouse (HM) virus species, and the Sin Nombre (SN) virus species. Infection with these viral agents is usually contracted through contact with the feces and urine of infected rodents, the primary reservoir of hantaviruses in nature.

Until recently, hantaviruses were thought to be responsible for causing human diseases collectively called hemorrhagic fever with renal syndrome (HFRS) in southeast Asia (HTN, SEO) and in western Europe (PUU), or not associated with human disease (PH). In May and June, 1993, an outbreak of an unknown disease presenting the abrupt onset of fever, myalgia, headache, cough and finally respiratory failure in the southwestern United States led to the description of the hantavirus pulmonary syndrome (HPS). A new hantavirus pathogenic for humans, the Sin Nombre (SN) virus was isolated and determined to be the causative agent of this disease. The primary reservoir for the Sin Nombre virus was found to be deer mice, *Peromyscus maniculatus*. Through Dec. 31, 1993, this disease was confirmed in 53 persons with a 60% fatality ratio.

The present invention provides a previously unreported species of hantavirus as the causative agent of a HPS occurrence in Florida. The virus responsible for this occurrence was isolated from cotton rats (*Sigmodon hispidus*) and represents a new and distinct serotype of hantavirus and is designated the Black Creek Canal hantavirus.

SUMMARY OF THE INVENTION

The present invention provides the discovery and isolation of a new virus. This virus is the etiologic agent responsible for the occurrence of a hantavirus Pulmonary Syndrome incident in Florida. Based upon genetic characteristics, this new virus is classified in the hantavirus family and represents a new species of hantavirus.

The present invention provides the isolated hantavirus, designated the Black Creek Canal hantavirus. Also provided are attenuated and inactivated derivatives of the new hantavirus. These isolated viruses can be used in methods of diagnosis of hantavirus infection or as vaccine components for prevention or treatment of hantavirus infection.

The invention also provides a method of detecting hantavirus infection in a sample, comprising detecting the presence in the sample of Black Creek Canal hantavirus. In this method, the presence of Black Creek Canal hantavirus can be detected by detecting a nucleic acid of Black Creek Canal hantavirus. A method of detecting current or previous hantavirus infection in a subject is also provided, comprising (a) contacting an antibody-containing sample from the subject with a Black Creek Canal hantavirus antigen; and (b) detecting the binding of the antigen and the antibody, the binding indicating the presence of the hantavirus.

The present invention also provides isolated nucleic acids and nucleic acid reagents which can be utilized to diagnose hantavirus infection. Purified polypeptides encoded by the nucleic acids are also provided. These polypeptides can be utilized in methods of diagnosis or as vaccine components for prevention or for treatment of hantavirus infection. Vectors are also provided which comprise the nucleic acids of the present invention. The vectors can be utilized in host expression systems to produce antigenic peptide reagents for diagnostic and prophylactic applications.

The present invention also provides purified antibodies that bind the hantavirus of the present invention or fragments thereof. These antibodies can be used in various diagnostic methods or as a therapeutic.

DETAILED DESCRIPTION OF THE INVENTION

Figure 1:
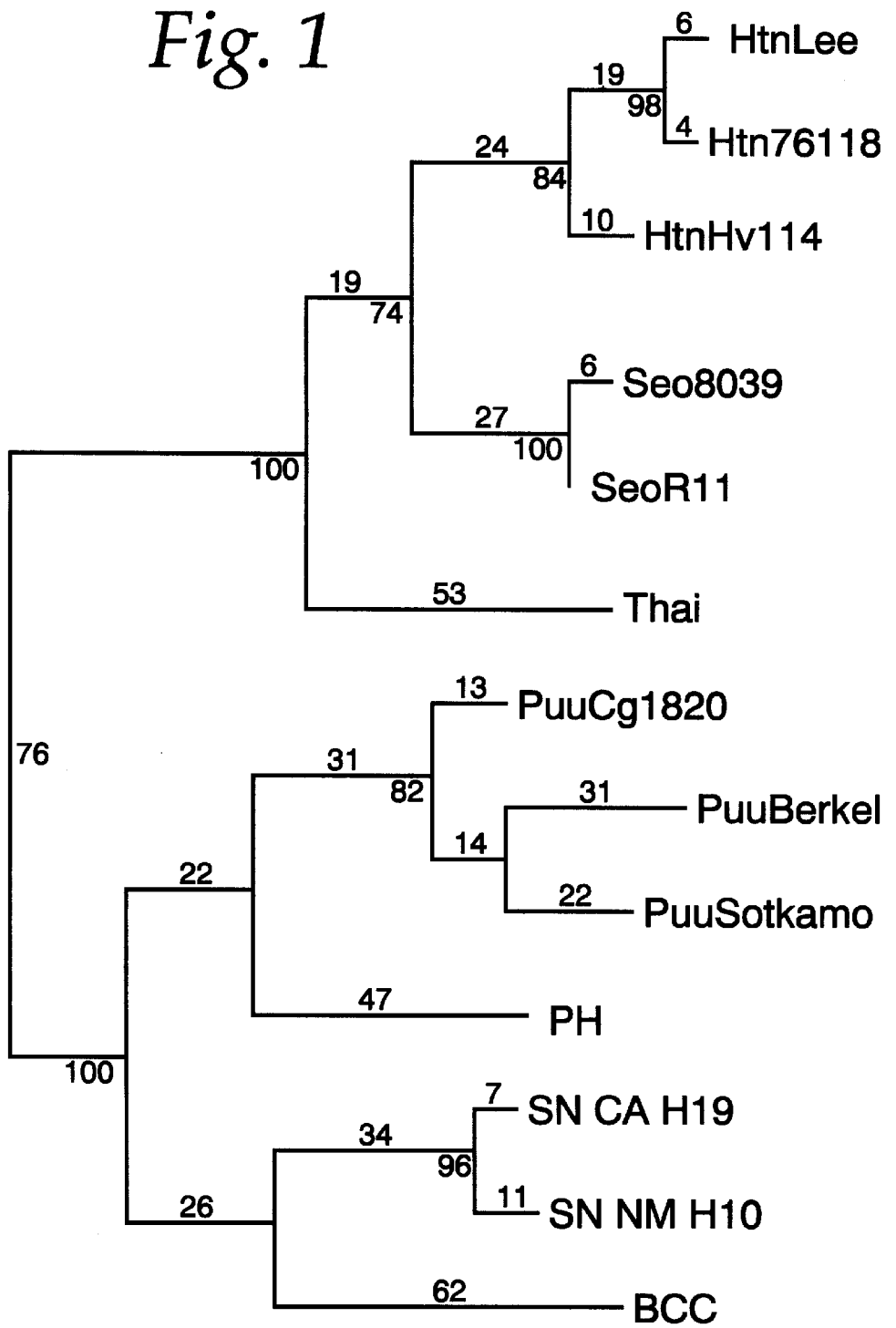
FIG. 1 is a phylogenetic tree showing the genetic relationship between Black Creek Canal hantavirus and other known hantaviruses. Nucleotide sequence differences among the 139 bp of PCR fragments of the M segment of Sigmodon virus isolate and previously characterized hantaviruses were analyzed by the weighted maximum parsimony method. A single most-parsimonius tree was obtained. Horizontal lengths are proportional to nucleotide step differences (indicated above lines). Vertical distances are for graphic representation only. Bootstrap confidence limits were calculated by 1000 repetitions of the analysis, and limits in excess of 50% are indicated in bold italics at appropriate branch points.

The present invention may be understood more readily by reference to the following detailed description of specific embodiments and the examples included therein. This description and the examples are intended as illustrative only since numerous modifications and variations therein will be apparent to those skilled in the art.

As used in the specification and in the claims, "a" can mean one or more, depending on the context in which it is used.

Isolated Black Creek Canal Hantavirus

The invention provides an isolated hantavirus, designated the "Black Creek Canal" hantavirus. "Isolated hantavirus" is defined as a viral preparation that is relatively free from other viral and cellular contaminants normally found in its natural environment, e.g., the lung, spleen, liver, or other tissues, or blood, sputum, urine, saliva, feces, or other fluids from infected rodents or humans. This viral preparation is contemplated to be sufficiently separated from other viral and cellular contaminants to be acceptable for use in a therapeutic or research setting. For example, a virus preparation that has been sufficiently separated from other viral and cellular contaminants so that it is useful in a diagnostic assay, such as polymerase chain reaction (PCR) or antibody detection assay, is "isolated." A hantavirus in culture (e.g., cell culture) is an "isolated" hantavirus. Thus, an intracellular hantavirus within cultured cells and extracellular hantavirus in the cell culture medium are examples of "isolated" hantavirus. Specific examples of isolation procedures for hantaviruses are provided in the Examples.

The Black Creek Canal hantavirus represents a new species of hantavirus. This virus is distinct from previously characterized hantaviruses both serologically and by its nucleic acid sequence. Whether a virus is of the species "Black Creek Canal" can be ascertained by methods which are known in the art, including, but not limited to polymerase chain reaction (e.g., RT-PCR), RNA hybridization, sequence analysis, and serologic classification.

More specifically, new isolates of Black Creek Canal hantavirus that exhibit limited genetic variation are still within the Black Creek Canal hantavirus species. A genetic variant of Black Creek Canal hantavirus is a hantavirus with less than 25% sequence divergence in all of the three gene segments (S, M or L) of the virus. The sequences provided herein as SEQ ID NOS:1 (S), 2 (M) and 3 (L) are the sequences against which the new isolate's S, M and L segments are compared. Thus, a virus with less than 25% sequence divergence in each of its three gene segments is within the same species and represents normal divergence from the present isolate of Black Creek Canal hantavirus.

Viruses identified that have more than 25% sequence divergence in any of the three gene segments when compared to the nucleotide sequence of any of the three gene segments of the present Black Creek Canal hantavirus are a distinct species of hantavirus as defined in the relevant art. Skilled practitioners in the field of hantavirus virology agree on this definition and this standard as evidenced by the report of the subcommittee on interrelationships among catalogued arboviruses (The American Society of Tropical Medicine and Hygiene, 43rd annual meeting, 1994, Cincinnati, Ohio, Report of the Subcommittee on Interrelationships Among Catalogued Arboviruses (SIRACA)). The report published by that subcommittee has defined a new hantavirus species (type) as a hantavirus which differs by at least 25% of its nucleotide sequence in at least one RNA segment compared all other known hantaviruses. Additionally, the fit in the evolutionary tree is consistent with type status (See, FIG. 1). This evolutionary tree analysis is performed using software packages widely available in the art such as PAUP. (Swofford, D. L., PAUP: Phylogenetic Analysis Using Parsimony, Version 3.0s. Computer program. Illinois Natural History Survey, Champaign, Ill.). An example of this analysis for categorizing viruses species is provided in the Examples. Sequence analyses for evolutionary classification such as this are common in the art and used to characterize the nucleic acid relatedness of various organisms, subcellular organelles such as mitochondria, and other viruses. (See e.g., Ou, C.-Y., et al., Molecular Epidemiology of HIV Transmission in a Dental Practice. Science 256:1165–1171 (1992)).

The SIRACA report further defines a subspecies (subtype) of a hantavirus species as a virus which differs from 5% to 24% in the nucleotide sequence in any of its three gene segments compared to the reference isolate. Viruses that have less than 4% divergence in the nucleotide sequence of each of the three gene segments are then within the same subspecies. Viruses classified as subspecies of the Black Creek Canal hantavirus species are considered minor variants of the species and are within the scope of the invention.

These definitions are recognized in the art as the standard by which hantaviruses are classified and are compatible with serological classification of these same viruses.

Detecting Hantavirus Infection

Also provided by the present invention is a method of detecting a hantavirus infection in a subject, comprising detecting the presence of the Black Creek Canal hantavirus in a sample from the subject. Examples of methods which can detect the presence of Black Creek Canal hantavirus or hantavirus antibodies in a sample include, but are not limited to, enzyme linked immunosorbent assays (ELISA), antigen capture, immunofluorescence assays (IFA) and other antigen-visualization techniques, plaque reduction and other neutralization tests, Western blots and other protein identification techniques, Northern blots, Southern Blots, polymerase chain reaction (PCR) and reverse-transcriptase polymerase chain reaction (RT-PCR), in situ hybridization techniques, solution hybridization techniques, ligase chain reaction (LCR), nucleic acid sequencing techniques, electrophoretic and non-electrophoretic identification of viral nucleic acids, radioimmunoassays such as radioimmunoprecipitation, microscopy techniques which can visualize the virus, cell culture and cell culture associated identification techniques such as hemagglutination and hemagglutination inhibition, and the like. In addition, any fragment of the Black Creek Canal hantavirus can be detected by methods such as these. Examples of ELISA, IFA, and RT-PCR detection methods used to detect the presence of Black Creek Canal hantavirus in samples are described below and provided in the Examples.

The presence of hantavirus infection can also be detected by detecting the presence of Black Creek Canal hantavirus in animal tissues or fluids. For example, artificially or naturally infected rodents can be the source of tissues or fluids which are analyzed for the presence of the hantavirus infection. Rodents used for detection attempts can be identified by first testing blood from the animals for the presence of hantavirus antibodies and then attempting virus isolation from the lungs or kidneys of those rodents found to have hantavirus-specific antibodies. Enzyme-linked immunosorbent assays (ELISA) performed on tissue samples such as these can initially test for the presence of the virus in these samples. Specific virus identification on antigen or antibody positive samples can then be performed by amplifying viral nucleic acids followed by nucleic acid sequencing those amplified products. An example of using *Sigmodon hispidus* lung tissues as the source of nucleic acids for amplification by RT-PCR can be found in the Examples.

Also provided is detecting the presence of the virus in cultured cells. An example of using ELISA, IFA, and PCR for detecting the presence of Black Creek Canal hantavirus in cultured Vero E6 cells can be found in the Examples.

Nucleic Acid Detection (Diagnosis) Methods

The invention also provides a method of detecting a hantavirus infection in a subject by detecting nucleic acids of Black Creek Canal hantavirus. The present invention provides reagents which can be used in a method of detecting the presence of the new virus in a subject, comprising detecting the presence of the nucleic acid encoded by the Black Creek Canal hantavirus. Based on the sequences provided herein, one can design reagents either to detect general hantavirus infection or a specific infection by the Black Creek Canal hantavirus described herein.

In particular, the present invention provides a method of detecting the presence of a Black Creek Canal hantavirus in a sample. For example, the RNA or cDNA derived from hantavirus RNA obtained from a sample can be sequenced and the sequence compared to the corresponding sequences for Black Creek Canal hantavirus. Examples of the sequences specific for Black Creek Canal hantavirus that can be used for comparison are provided in the Sequence Listing. Other nucleic acids unique (specific) to Black Creek Canal hantavirus can be readily ascertained by comparing the sequence of the nucleic acid in question to sequences catalogued in GenBank, or any other sequence database, using the computer programs such as DNASIS (Hitachi Engineering, Inc.) or Word Search or FASTA of the Genetics Computer Group (GCG) (Madison, Wis.), which search the catalogued nucleotide sequences for similarities to the nucleic acid in question. If the sequence does not match any of the known sequences, it is unique. Thus, if the sequence of the nucleic acid obtained from the sample varies by less than 25% in the S, M and L segments from the present reference sequences,(SEQ ID NOS:, 1, 2, and 3), the infection is by Black Creek Canal hantavirus.

More specifically, the method of detecting Black Creek Canal hantavirus in a sample can comprise reverse transcribing viral RNA to synthesize a complementary DNA sequence followed by amplification of the DNA from the sample using nucleic acid primers for the Black Creek Canal hantavirus and detecting the presence a nucleic acid unique to Black Creek Canal hantavirus, the presence of a nucleic acid unique to Black Creek Canal hantavirus indicating the presence of the Black Creek Canal hantavirus in the sample. The detection of a nucleic acid unique to Black Creek Canal hantavirus can be by the detection of amplification product when species specific primers are used. The detection of a nucleic acid unique to Black Creek Canal hantavirus can be by direct hybridization utilizing a species-specific oligonucleotide probe, by a restriction fragment length polymorphism, or by sequencing and sequence comparison when non-species-specific primers are used. The primers can, for example, be derived from the nucleotide sequences set forth in the Sequence Listing as SEQ ID NO:1 through SEQ ID NO:3, or the sequences complementary thereto. Standard criteria for selection of sequences for primer development are applicable. The crucial requirement is that the primers be such that an amplification protocol using them can distinguish Black Creek Canal hantavirus nucleic acids from the nucleic acids of other species. This is not to say that non-specific amplification will not occur, but that the skilled artisan can distinguish non-specific amplification from the amplification of nucleic acids of Black Creek Canal hantavirus, for example, by following amplification with the use of a specific probe. Thus, the primers themselves need not be species specific. These generic primers can be derived from the genomic segments of other hantaviruses.

For example, the present invention also provides a method of detecting the presence of hantavirus species other than Black Creek Canal hantavirus in a sample, comprising amplifying the nucleic acids from the sample using primers derived from Black Creek Canal hantavirus that amplify the nucleic acids and detecting the presence of a nucleic acid unique to the genus hantavirus in the amplification product, the presence of a hantavirus nucleic acid indicating the presence of the hantavirus in the sample. The generic primers used in this method can also be derived from the nucleotide sequences set forth in the Sequence Listing as SEQ ID NO:1 through SEQ ID NO:3, or the sequence complementary thereto. Thus, the amplified nucleic acids can be unique to the Black Creek Canal hantavirus species as described above or generic to other hantavirus species as well. The choice of primer will depend on which result is sought, and is based on a straight forward comparison of the sequences from the relevant hantaviruse(s).

Specific examples of oligonucleotide primers are provided herein. Examples of primers are set forth in the Sequence Listing as SEQ ID NO:3; SEQ ID NO:4; SEQ ID NO:5, SEQ ID NO:6, and SEQ ID NO:7. Such primers are suitable for use in the PCR amplification methods provided by the invention and described herein. Methods of using primers to clone and sequence nucleic acids of hantaviruses are known in the art. A specific example of the use of these primers to amplify a hantavirus nucleic acid encoding the nucleocapsid protein is provided in U.S. Ser. No. 08/133, 591, filed Oct. 7, 1993.

The oligonucleotides chosen for use as primers in amplification of template DNA or reverse transcription of viral RNA, or for use as a probe in a hybridization and detection assay can vary in length and stringency conditions. The oligonucleotides used as primers are typically between 12 and 30 nucleotides in length with a preferable range of 15–25 nucleotides. One skilled in the art, however, will readily appreciate that there is no standard length or stringency for optimal polymerase chain reaction amplification, reverse transcription, or hybridization, but that an optimal length for a particular application is readily determined. (PCR Technology, Principles and Applications for DNA Amplification, H. A. Erlich, Ed. (1989)). Several computer software programs are available to facilitate primer design. (Lowe, T., Sharefkin, J., Yang, S. Q., and Dieffenbach, C. W. A. "Computer program for selection of oligonucleotide primers for polymerase chain reactions." Nuc. Acids. Res. 18:1757–1761 (1991) and RT-PCR, Methods and Applications Book 1. Clontech Laboratories, Inc. (1991)).

The amplification techniques contemplated in the present methods include polymerase chain reaction (PCR), reverse-transcriptase polymerase chain reaction (RT-PCR), or ligase chain reaction (LCR). Alternatively, the presence of a Black Creek Canal hantavirus can be detected by directly hybridizing a nucleic acid probe specific for the Black Creek Canal hantavirus to nucleic acids from a sample. Furthermore, the nucleotide sequence could be amplified prior to hybridization by the methods described above.

Alternative nucleic acid detection methods, such as LCR, involve the use of mismatch probes, i.e., probes which are fully complementary with the target except a mutation. The target sequence is then allowed to hybridize both with oligonucleotides which are fully complementary and with oligonucleotides containing a mismatch, under conditions which will distinguish between the two. By manipulating the reaction conditions, it is possible to obtain hybridization only where there is full complementarity. If a mismatch is present there is significantly reduced hybridization.

The polymerase chain reaction (PCR) and reverse transcriptase PCR (RT-PCR) are techniques that amplify specific nucleic acid sequences with remarkable efficiency. Repeated cycles of denaturation, primer annealing and primer extension carried out with a polymerase, e.g., the heat stable enzyme Taq polymerase, leads to exponential increases in the concentration of desired nucleic acid sequences. Given a knowledge of the nucleotide sequence of the Black Creek Canal hantavirus as provided herein, synthetic oligonucleotides (primers) can be prepared which are complementary to sequences which flank the nucleic acid of interest. Each oligonucleotide can be totally or partially complementary to one of the two strands in amplifying double stranded nucleic acids, or a primer can be partially or totally complementary to a strand of single stranded nucleic acid obtained from a sample. The nucleic acid can be denatured at high temperatures (e.g., 95° C.) and then reannealed in the presence of a large molar excess of oligonucleotide primers. The oligonucleotide primers, oriented with their 3' ends pointing towards each other, hybridize to opposite strands of the target sequence and prime enzymatic extension along the nucleic acid template in the presence of four deoxyribonucleotide triphosphates. The end product is then denatured again for another cycle. After this cycle has been repeated several times, amplification of a nucleic acid segment by more than one million-fold can be achieved. The resulting nucleic acid may then be directly sequenced in order to locate any genetic alteration or mutation.

In PCR, denaturation of strands usually takes place at 94° C. and extension from the primers is usually at 72° C. The annealing temperature varies according to the sequence under investigation. Examples of reaction times are: 20 min denaturing; 35 cycles of 2 min, 1 min, and 1 min for annealing, extension and denaturation, respectively; and finally, a 5 min extension step.

In yet another method, PCR may be followed by restriction endonuclease digestion with subsequent analysis of the resultant products. Nucleotide substitutions can result in the gain or loss of a specific restriction endonuclease site. The gain or loss of a restriction endonuclease recognition site facilitates the detection of the organism using restriction fragment length polymorphism (RFLP) analysis or by detection of the presence or absence of a polymorphic restriction endonuclease site in a PCR product that spans the sequence of interest. This technique may be used to identify a particular species of hantavirus based on the presence or absence of nucleotide variations at particular sites. (See, e.g., Strachan, T. The Human Genome. Ed. A. P. Read and T. Brown, Bios Scientific Publishers, Oxford, England, pg. 63–64 (1992)).

For RFLP analysis, RNA is obtained, for example, from a tissue sample or a fluid sample such as serum from the subject or sample suspected of containing a hantavirus. DNA amplified from reverse-transcribed RNA is digested with a restriction endonuclease, and subsequently separated on the basis of mass by electrophoresis. For example, the Southern blot technique can then be used to detect, by hybridization with labeled probes, the products of endonuclease digestion. The patterns obtained from the Southern blot can then be compared. Using such an approach, nucleic acids specific for hantaviruses, and in particular the Black Creek Canal hantavirus, can be detected.

Creation of additional restriction sites by nucleotide substitutions can be readily calculated by reference to the genetic code and a list of nucleotide sequences recognized by restriction endonucleases. Single strand conformational analysis (SSCA) offers a relatively quick method of detecting sequence changes which may be appropriate in at least some instances.

Serological Detection
Detecting Antibody With Antigen

The current invention provides methods of detecting current or previous hantavirus infection in a subject, comprising the steps of a) contacting an antibody-containing sample from a subject with a Black Creek Canal hantavirus antigen; and b) detecting the binding of the antigen and the antibody, the binding indicating the presence of the hantavirus. The infection detected can be Black Creek Canal hantavirus infection or it can be infection by another species of hantavirus.

In the present method of detecting the presence of a current or previous hantavirus infection, the Black Creek Canal hantavirus antigen can be a polypeptide encoded by the nucleic acid set forth in the Sequence Listing as SEQ ID NO:1, a polypeptide encoded by the nucleic acid set forth in the Sequence Listing as SEQ ID NO:2 or a polypeptide encoded by the nucleic acid set forth in the Sequence Listing as SEQ ID NO:3. In the present method of detecting the presence of a current or previous hantavirus infection, the Black Creek Canal hantavirus antigen can alternatively be the isolated Black Creek Canal hantavirus.

The nucleic acid set forth in SEQ ID NO:2 encodes two surface glycoproteins of the hantavirus, G1 and G2. Thus, the antigen of the present method can be either of these proteins or an antigenic polypeptide fragment of either protein. The nucleic acid set forth in SEQ ID NO:1 encodes the nucleocapsid protein (N) of the hantavirus and a potential, approximately 6 kD, protein of hantavirus. Thus, the antigen of the present method can be the nucleocapsid protein, the potential 6 kD protein, or antigenic fragments thereof. The nucleic acid set forth in SEQ ID NO:3 encodes the viral polymerase protein. Thus, the antigen of the present method can be this protein or an antigenic polypeptide fragment thereof. In addition, any other antigenic polypeptide encoded by the nucleic acids set forth as SEQ ID NOS:1–3 can be the antigen of the present detection assay.

For example, antigens can be selected that will distinguish an antibody produced in response to the presence of hantavirus from one of the groups of hantaviruses (Haantan/Thai/Seoul main branch) depicted in the phylogenetic tree of FIG. 1, from an antibody produced in response to infection with a hantavirus from the other group of hantaviruses (Puumala/Prospect Hill/Sin Nombre/Black Creek Canal main branch) depicted in the phylogenetic tree. The nucleocapsid protein (for example as encoded by SEQ ID NO:1) or antigenic fragments thereof are examples of such antigens. Other antigens can be selected that can distinguish between infections by hantaviruses in sub-branches of the phylogenetic tree. Thus, the G1 protein (for example as encoded by SEQ ID NO:2) or fragments thereof from hantaviruses that have sigmodon-like rodent hosts can be used to distinguish antibodies that are produced from infection by hantaviruses having sigmodon-like hosts (e.g., Black Creek Canal hantavirus) from antibodies produced against hantaviruses having peromyscus-like hosts (e.g., Sin Nombre).

In one diagnostic setting, the present nucleic acids can first be used in an initial broad screening for the presence of hanatvirus by using two nucleocapsid antigens, each specific for the group of hantaviruses in one or the other of the two main branches of the phylogenetic tree to detect antibodies produced in response to the hantaviruses in both branches. This screening step will establish the presence of hantavirus antibodies, and will determine which of the two main groups of hantaviruses the antibody was produced against. Once the broad grouping of the hantavirus is known to be, for example, from the Puumala/Prospect Hill/Sin Nombre/Black Creek Canal branch, a G1 antigen or antigenic fragment specific for the Black Creek Canal hantavirus can be used to detect current or previous Black Creek Canal hantavirus infection. In this context, the terms "specific antigen" or "specific antigenic fragment" means that the antigen/fragment binding to antibodies produced against the target hantavirus species or target group of hantavirus species can be distinguished (e.g., by its higher affinity) from its binding to antibodies produced against non-target viruses.

Detecting Antigen with Antibody/Ligand

Another example of a method of hantavirus detection provided by the present invention is performed by contacting a hantavirus-containing fluid or tissue sample from the subject with an amount of a purified antibody which binds the hantavirus antigen as defined herein, and detecting the reaction of the ligand with the antigen, the binding indicating the presence of hantavirus in the sample.

In the method of detecting the presence of a hantavirus in a sample, the antibody can be an antibody which specifically binds to Black Creek Canal hantavirus. Additionally, the antibody can be one which binds to nucleocapsid protein or other antigenic polypeptide encoded by the nucleic acid set forth in the Sequence Listing as SEQ ID NO:1. The antibody can be one which binds to either the G1 or G2 proteins or other antigenic polypeptide encoded by the nucleic acid set forth in the sequence Listing as SEQ ID NO:2. The antibody can be one which specifically binds to the polypeptide encoded by the nucleic acid set forth in the sequence Listing as SEQ ID NO:3 or antigenic fragments thereof. For the detection of hantavirus, the antibody should be specific for hantavirus. That is, it should bind hantavirus antigens with greater affinity than it binds non-hantavirus antigens. Thus, the presence of an antibody/hantavirus antigen complex can be distinguished from binding with a non-hantavirus antigen if a hantavirus-specific antibody is used. For the detection of Black Creek Canal hantavirus, the antibody should be specific for Black Creek Canal hantavirus. That is, it should bind Black Creek Canal hantavirus-specific antigens with greater affinity than it binds non-Black Creek Canal hantavirus antigens, so that the presence of Black Creek Canal hantavirus in a sample can be distinguished from other hantaviruses or a non-hantavirus antigen if a Black Creek Canal hantavirus-specific antibody is used.

It is contemplated that the antigens or antigenic fragments detected by the antibody will be exposed on intact cells containing the antigen, or will be available for binding to antibodies only after cells containing the antigens are lysed. As contemplated herein, the antibody includes any ligand which binds the antigen or antigenic fragment, for example, an intact antibody, a fragment of an antibody or another reagent that specifically binds the antigen. The fluid sample of this method can comprise any body fluid which would contain the antigen or a cell containing the antigen, such as blood, plasma, serum, sputum, mucus, saliva and urine. Other examples of body fluids include gastric juice, lymph and the like. The sample can also be solubilized or nonsolubilized tissue samples from the subject or solubilized or nonsolubilized cultured cells. The sample can also be supernatant from incubated tissue samples or cultured cells.

There are numerous immunodiagnostic methods that can be used to detect antigen or antibody as the following non-inclusive examples illustrate.

ELISA

Enzyme immunoassays such as immunofluorescence assays (IFA), enzyme linked immunosorbent assays (ELISA) and immunoblotting can be readily adapted to accomplish the detection of the antigen or antibody. An ELISA method effective for the detection of the antigen, for example, can be as follows: (1) bind the antibody to a substrate; (2) contact the bound antibody with a fluid or tissue sample containing the antigen; (3) contact the above with a secondary antibody bound to a detectable moiety (e.g., horseradish peroxidase enzyme or alkaline phosphatase enzyme); (4) contact the above with the substrate for the enzyme; (5) contact the above with a color reagent; (6) observe color change. The above method can be readily modified to detect antibody as well as antigen.

Competitive Inhibition Assay

Another immunologic technique that can be useful in the detection of current or previous hantavirus infection utilizes monoclonal antibodies (MAbs) for detection of antibodies that specifically bind hantavirus antigen. Briefly, sera or other body fluid from the subject is reacted with the antigen bound to a substrate (e.g. an ELISA 96-well plate). Excess sera is thoroughly washed away. A labeled (enzyme-linked, fluorescent, radioactive, etc.) monoclonal antibody is then reacted with the previously reacted antigen-serum antibody complex. The amount of inhibition of monoclonal antibody binding is measured relative to a control (no patient serum antibody). The degree of monoclonal antibody inhibition can be a specific test for a particular species or subspecies or variety or strain since it is based on monoclonal antibody binding specificity. MAbs can also be used for detection directly in cells by IFA.

Micro-Agglutination Assay

A micro-agglutination test can also be used to detect the presence of antibodies in a subject. Briefly, latex beads (or red blood cells) are coated with the antigen and mixed with a sample from the subject, such that antibodies in the tissue or body fluids that are specifically reactive with the antigen crosslink with the antigen, causing agglutination. The agglutinated antigen-antibody complexes form a precipitate, visible with the naked eye or detectable by a spectrophotometer. In a modification of the above test, antibodies specifically reactive with the antigen can be bound to the beads and antigen in the tissue or body fluid thereby detected.

Sandwich Assay/Flow Cytometry/Immunoprecipitation

In addition, as in a typical sandwich assay, the antibody can be bound to a substrate and contacted with the antigen. Thereafter, a labeled secondary antibody is bound to epitopes not recognized by the first antibody and the secondary antibody is detected. Since the present invention provides antigens from the Black Creek Canal hantavirus for the detection of current or previous infection with hantavirus, generally, or Black Creek Canal hantavirus, specifically, other serological methods such as flow cytometry and immunoprecipitation can also be used as detection methods.

In the diagnostic methods taught herein, the antigen can be bound to a substrate and contacted by a fluid sample such as serum, urine, saliva or gastric juice. This sample can be taken directly from the patient or animal, or in a partially purified form. In this manner, antibodies specific for the antigen (the primary antibody) will specifically bind with the bound antigen. Thereafter, a secondary antibody bound to, or labeled with, a detectable moiety can be added to enhance the detection of the primary antibody. Generally, the secondary antibody or other ligand which binds specifically with a different epitope of the antigen or nonspecifically with the ligand or bound antibody, will be selected for its ability to bind with multiple sites on the primary antibody. Thus, for example, several molecules of the secondary antibody can bind with each primary antibody, making the primary antibody more detectable.

Detectable Moieties

The detectable moiety will allow visual detection of a precipitate or a color change, visual detection by microscopy, or automated detection by spectrometry, radiometric measurement or the like. Examples of detectable moieties include fluorescein and rhodamine (for fluorescence microscopy), horseradish peroxidase (for either light or electron microscopy and biochemical detection), biotin-streptavidin (for light or electron microscopy) and alkaline phosphatase (for biochemical detection by color change). The detection methods and moieties used can be selected, for example, from the list above or other suitable examples by the standard criteria applied to such selections (Harlow, E, et al., Antibodies: A Laboratory Manual, Cold Spring Harbor Laboratory, Cold Spring Harbor, New York, pg. 53–281 (1988)).

Nucleic Acids

The present invention provides the isolated nucleic acids comprising the nucleotide sequences set forth in the Sequence Listing as SEQ ID NO:1, SEQ ID NO:2, and SEQ ID NO:3. The cDNA sequence shown in SEQ ID NO:1 is a 1989 nucleotide sequence complementary to RNA derived from the S segment of the genome of an isolate of the new species Black Creek Canal hantavirus. The cDNA sequence shown in SEQ ID NO:2 is a 3668 nucleotide sequence complementary to RNA derived from the M segment of the genome of an isolate of the Black Creek Canal hantavirus of the present invention. The cDNA sequence shown in SEQ ID NO:3 is a 410 nucleotide sequence complementary to RNA derived from part of the L segment of the genome of a Black Creek Canal hantavirus of the present invention. The sequences listed as SEQ ID NO:1, 2, and 3, therefore correspond to the positive strand of the nucleic acid. The RNA molecules packaged in the virion are the negative strand. The invention includes DNA having the recited sequences and its complement, and RNAs which correspond to or are complementary to the DNAs.

The present invention provides a partial sequence of the L segment. Given the sequence set forth in the Sequence Listing as SEQ ID NO:3, the complete L segment can readily be cloned. Methods used to isolate a nucleic acid encoding a complete L segment include, but are not limited to, screening the genome of a Black Creek Canal hantavirus species by nucleic acid hybridization methods or through polymerase chain reaction (PCR) techniques. A skilled artisan will readily appreciate the sequence of SEQ ID NO:3 provides numerous possible primers for nucleic acid amplification as well as nucleic acids which can be used as specific probes to clone and identify the complete L segment. Materials suitable for screening include, but are not limited to, cDNA libraries of the appropriate hantavirus species cloned into lambda, cosmid, yeast, mammalian, or plasmid cloning vectors, DNA isolated and subjected to Southern blot analysis, RNA isolated and subjected to Northern blot analysis, and isolated DNA or RNA used as a template for PCR.

By "isolated nucleic acid" is meant nucleic acid molecules that are separated from at least some of the other nucleic acids or other viral components found in the naturally occurring hantavirus, such as viral proteins. Separation techniques for isolating nucleic acids from viruses, as well as from other organisms, are very well known in the art and include phenol extraction followed by ethanol precipitation and rapid solubilization of viruses and other cells by organic solvent or detergents. (See, e.g., Sambrook precipitation and rapid solubilization of viruses and other cells by organic solvent or detergents. (See, e.g., Sambrook et al., Molecular Cloning: A Laboratory Manual. 2nd Ed., Cold Spring Harbor Laboratory, Cold Spring Harbor, N.Y. (1989)). The nucleic acids of the present invention can include positive and negative strand RNA as well as DNA and include genomic and subgenomic nucleic acids found in the naturally occurring organism. The nucleic acids contemplated by the present invention include negative stranded vRNA of the genome, complementary positive stranded cRNA and mRNA, and complementary cDNA produced therefrom and any nucleic acid which can hybridize to or encode the Black Creek Canal hantavirus. The nucleic acids of the present invention specifically include RNA from the three genome segments of Black Creek Canal hantavirus designated small (S), medium (M) and large (L), and nucleic acids complementary thereto.

The present invention also provides isolated nucleic acids that hybridize with and amplify the nucleic acids comprising the nucleotide sequences set forth in the Sequence Listing as SEQ ID NO:1, SEQ ID NO:2, and SEQ ID NO:3, and the sequences complementary thereto. As contemplated herein, the hybridizing nucleic acids do not include any nucleic acids that are currently known to exist in other hantavirus species or non-hantavirus species.

An isolated nucleic acid capable of amplifying all regions of the genome of the Black Creek Canal hantavirus of the present invention is contemplated. Such a nucleic acid could be a species-specific or genus-specific primer derived by sequence comparison from one of the three segments of the present Black Creek Canal hantavirus. The sequences can be selected based a nucleotide sequence comparison with presently known hantaviruses. Available computer programs can be used to compare the sequence to select the most appropriate sequences for amplification and hybridization and this type of primer selection is entirely routine in the art. For example, hybridization primers can readily be designed using the primer analysis software OLIGO® (National Biosciences, Inc.), and oligonucleotides identified by this type of analysis can readily be compared with known sequences on GenBank and EMBL using the nucleotide sequence analysis software DNASIS (Hitachi Engineering, Ltd.). Sequence analysis software such as DNASIS, as well as others, such as GCG (Genetics Computer Group, Madison, Wis.), can scan the entire sequence databases in a matter of minutes to determine whether sequences similar to or identical to the nucleic acids designed for hybridization oligonucleotides have previously been disclosed.

In particular, an isolated nucleic acid that selectively hybridizes with (or selectively amplifies) the nucleic acids set forth in SEQ ID NOS:1–3 under stringent conditions and comprises at least 10 nucleotides complementary to a sequence set forth in SEQ ID NO:1, 2, or 3 is provided. The hybridizing nucleic acid should have at least 70% complementarity with the segment of the nucleic acid of SEQ ID NOS:1–3 to which it hybridizes. As used herein to describe nucleic acids, the term "selectively hybridizes" excludes the occasional randomly hybridizing nucleic acids and thus has the same meaning as "specifically hybridizing". The hybridizing nucleic acids can be used, for example, as probes or primers for detecting an isolate of the Black Creek Canal hantavirus species that has the nucleic acid to which the primer or probe hybridizes.

The selectively hybridizing nucleic acids of the invention can have at least 70%, 80%, 85%, 90%, 95%, 97%, 98% and 99% complementarity with the segment of the sequence to which it hybridizes. The nucleic acids can be at least 12, 50, 100, 150, 200, 300, 500, 750, 1000, 2000, 3000, 4000 or 6000 nucleotides in length. Thus, the nucleic acid can be a coding sequence for the Black Creek Canal hantavirus or antigens thereof that can be utilized to produce an antigenic protein or protein fragment, or it can be used as a probe or primer for detecting the presence of hantavirus. If used as primers, the invention provides compositions including at least two nucleic acids which hybridize with different regions so as to amplify a desired region. Depending on the length of the probe or primer, target region can range between 70% complementary bases and full complementarity and still hybridize under stringent conditions. For example, for the purpose of diagnosing the presence of the Black Creek Canal hantavirus, the degree of complementarity between the hybridizing nucleic acid (probe or primer) and the sequence to which it hybridizes (e.g., hantaviral RNA from a sample) is at least enough to distinguish hybridization with a nucleic acid from related virus (e.g., a previously existing strain such as Hantaan, Prospect Hill, Seoul, Sin Nombre or Puumala strains). The invention provides examples of nucleic acids unique to the Black Creek Canal hantavirus in the Sequence Listing so that the degree of complementarity required to distinguish selectively hybridizing from nonselectively hybridizing nucleic acids under stringent conditions can be clearly determined for each nucleic acid.

Additionally, the nucleic acids of the invention can have at least 80% similarity with the coding nucleotides of SEQ ID NOS:1–3 that are not subject to the degeneracy of the genetic code, i.e., with the non-"wobble" nucleotides (the wobble nucleotides usually being the third nucleotide in a codon) in the coding sequence. Preferably, the nucleic acids will have 90%, or more preferably, 95%, or even more preferably, 99% homology with the coding nucleotides of SEQ ID NOS:1–3 that are not subject to the degeneracy of the genetic code.

"Stringent conditions" refers to the hybridization conditions used in a hybridization protocol, for example, RNA/RNA hybridization, as in the genogrouping method, or in the primer/template hybridization in a PCR reaction. In general, these conditions should be a combination of temperature and salt concentration for washing chosen so that the denaturation temperature is approximately 5°–20° C. below the calculated $T_m$ (melting/denaturation temperature) of the hybrid under study. The temperature and salt conditions are readily determined empirically in preliminary experiments in which samples of reference RNA are hybridized to the primer nucleic acid of interest and then amplified under conditions of different stringencies. The stringency conditions are readily tested and the parameters altered are readily apparent to one skilled in the art. For example, $MgCl_2$ concentrations used in the reaction buffer can be altered to increase the specificity with which the primer binds to the template, but the concentration range of this compound used in hybridization reactions is narrow, and therefore, the proper stringency level is easily determined. For example, hybridizations with oligonucleotide probes 18 nucleotides in length can be done at 5°–10° C. below the estimated $T_m$ in 6X SSPE, then washed at the same temperature in 2X SSPE (see, e.g., Sambrook et al., Molecular Cloning: A Laboratory Manual. 2nd Ed., Cold Spring Harbor Laboratory, Cold Spring Harbor, New York (1989)). The $T_m$ of such an oligonucleotide can be estimated by allowing 2° C. for each A or T nucleotide, and 4° C. for each G or C. An 18 nucleotide probe of 50% G+C would, therefore, have an approximate $T_m$ of 54° C. Likewise, the starting salt concentration of an 18 nucleotide primer or probe would be about 100–200 mM. Thus, stringent conditions for such an 18 nucleotide primer or probe would be a $T_m$ of about 54° C. and a starting salt concentration of about 150 mM and modified accordingly by preliminary experiments. $T_m$ values can also be calculated for a variety of conditions utilizing commercially available computer software (e.g., OLIGO®).

Modifications to the nucleic acids of the invention are also contemplated as long as the essential structure and function of the polypeptide encoded by the nucleic acids is maintained. Likewise, fragments used as primers can have substitutions so long as enough complementary bases exist for selective amplification (Kunkel et al., *Methods Enzymol.* 154:367 (1987)) and fragments used as probes can have substitutions so long as enough complementary bases exist for hybridization with the reference sequence can be distinguished from hybridization with other sequences.

In addition, fragments of the nucleic acids described herein can be selected to be identical to or highly similar to nucleotide sequences present in other human or animal hantaviruses. Such a nucleotide sequence shared with other hantaviruses can be used, for example, to simultaneously detect related strains or in a construct for generating a multiprotective vaccine.

Antigen

Purified antigenic polypeptides, or antigenic fragments thereof, encoded by the nucleic acids of the present invention are also contemplated. As used herein, "purified" means the antigen is sufficiently free of contaminants or cell components with which the antigen normally occurs to distinguish the antigen from the contaminants or components. It is not contemplated that "purified" necessitates having a preparation that is technically totally pure (homogeneous), but purified as used herein means the antigen (or antibody or nucleic acid) is sufficiently separated from contaminants or cell components with which the antigen normally occurs to provide the antigen (or antibody or nucleic acid) in a state where it can be used in an assay, such as an ELISA. As used herein "antigen" and "antigenic" refer to a polypeptide that induces an immune response. As used herein, "encoded" is meant to include negative stranded genomic vRNA capable of transcription into positive strand cRNA or mRNA and includes the viral polypeptides specifically encoded by positive sense cRNA or mRNA produced synthetically or found in the naturally occurring virus or organism containing the virus. Purified antigenic proteins of Black Creek Canal hantavirus and antigenic polypeptide fragments thereof, as well as purified Black Creek Canal hantavirus are also referred to herein as "the antigen" or "Black Creek Canal hantavirus antigen."

Specific examples of the Black Creek Canal hantavirus antigens of the invention are the proteins or fragments of proteins encoded by the nucleotide sequences set forth in the Sequence Listing as SEQ ID NO:1, SEQ ID NO:2, and SEQ ID NO:3. It is already well established that the G1, G2, and N proteins of hantaviruses are antigenic. As is typical, it is expected that fragments of these proteins will possess epitopes of the protein that are either specific for the Black Creek Canal hantavirus or for other hantaviruses. These epitopes and the polypeptide fragments containing them can be readily determined by the very well known techniques of epitope mapping and conformational dependency analysis.

Naturally, relevant polypeptides are only those encoded by the plus strands. The purified polypeptides can be tested to determine their antigenicity and specificity by the methods taught herein. Antigenic fragments of the antigen can be synthesized directly or obtained by chemical or mechanical disruption of the virus or larger polypeptides. The antigenic polypeptides of the present invention can also be recombinant proteins obtained by cloning nucleic acids encoding the polypeptide in an expression system capable of producing the antigenic polypeptide or fragments thereof. An antigenic fragment is defined as an amino acid sequence of at least about 5 consecutive amino acids derived from the amino acid sequence.

Once the amino acid sequence of an antigenic protein of the Black Creek Canal hantavirus is known or deduced, it is also possible to synthesize, using standard peptide synthesis techniques, peptide fragments chosen to be homologous to immunoreactive regions of the larger antigen and to modify these fragments by inclusion, deletion or modification of particular amino acids residues in the derived sequences. The amino acid sequences of the present polypeptides can contain an immunoreactive portion of the antigen attached to sequences designed to provide for some additional property, such as solubility. The amino acid sequences of the polypeptides can also include sequences in which one or more amino acids have been substituted with another amino acid to provide for some additional property, such as to remove/add amino acids capable of disulfide bonding, to increase its antigenicity, bio-longevity, or alter enzymatic activity. Thus, synthesis or purification of an extremely large number of peptides derived from the antigen is possible. In any case, the peptide must possess a bioactive property, such as antigenicity, immunoreactivity, immunogenicity, etc.

A purified virus or Black Creek Canal hantavirus antigen bound to a substrate and a ligand specifically reactive with the virus or viral antigen are also contemplated. Such a purified ligand specifically reactive with the virus or viral antigen can be an antibody. The antibody can be a monoclonal antibody obtained by standard methods and as described herein.

Determining Antigenicity and Immunogenicity

The purified polypeptide fragments thus obtained can be tested to determine their antigenicity (immunoreactivity), immunogenicity and specificity and effective amount. Briefly, various concentrations of a putative immunogenically specific fragment are prepared and administered to an animal and the immunological response (e.g., the production of antibodies or cell mediated immunity) of an animal to each concentration is determined. The amounts of antigen administered depend on the subject, e.g. a human or a rodent, the condition of the subject, the size of the subject, etc. Thereafter an animal so inoculated with the antigen can be exposed to the virus to test the potential vaccine effect (protective immunogenicity) of the specific antigenic fragment. The specificity of a putative immunogenic fragment can be ascertained by testing sera, other fluids or lymphocytes from the inoculated animal for cross reactivity with other closely related hantaviruses.

Vectors and Hosts

A vector comprising the nucleic acids of the present invention is also provided. The vectors of the invention can be in a host (e.g., cell line or transgenic animal) that can express the antigenic polypeptide fragments contemplated by the present invention. The present invention provides a vector comprising a nucleic acid having the nucleotide sequences set forth in the Sequence Listing as SEQ ID NO:1, SEQ ID NO:2, or SEQ ID NO:3, or a nucleic acid complementary to or capable of hybridizing with the reference nucleic acids.

There are numerous *E. coil* (*Escherichia coli*) expression vectors known to one of ordinary skill in the art useful for the expression of the antigen. Other microbial hosts suitable for use include bacilli, such as *Bacillus subtilis*, and other enterobacteriaceae, such as *Salmonella, Serratia*, and various Pseudomonas species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary an amino terminal methionine can be provided by insertion of a Met codon 5' and in-frame with the antigen. Also, the carboxy-terminal extension of the antigen can be removed using standard oligonucleotide mutagenesis procedures.

Additionally, yeast expression can be used. There are several advantages to yeast expression systems. First, evidence exists that proteins produced in a yeast secretion systems exhibit correct disulfide pairing. Second, post-translational glycosylation is efficiently carried out by yeast secretory systems. The *Saccharomyces cerevisiae* pre-pro-alpha-factor leader region (encoded by the MF$\alpha$-1 gene) is routinely used to direct protein secretion from yeast (Brake, A. J. et al., $\alpha$-factor-directed synthesis and secretion of mature foreign proteins in *Saccharomyces cerevisiae*. Proc. Nat. Acad. Sci. 81:4642–4646 (1984)). The leader region of pre-pro-alpha-factor contains a signal peptide and a pro-segment which includes a recognition sequence for a yeast protease encoded by the KEX2 gene: this enzyme cleaves the precursor protein on the carboxyl side of a Lys-Arg dipeptide cleavage-signal sequence. The antigen coding sequence can be fused in-frame to the pre-pro-alpha-factor leader region. This construct is then put under the control of a strong transcription promoter, such as the alcohol dehydrogenase I promoter or a glycolytic promoter. The antigen coding sequence is followed by a translation termination codon which is followed by transcription termination signals. Alternatively, the antigen coding sequences can be fused to a second protein coding sequence, such as Sj26 or $\beta$-galactosidase, used to facilitate purification of the fusion protein by affinity chromatography. The insertion of protease cleavage sites to separate the components of the fusion protein is applicable to constructs used for expression in yeast. Efficient post translational glycosylation and expression of recombinant proteins can also be achieved in Baculovirus systems.

Mammalian cells permit the expression of proteins in an environment that favors important post-translational modifications such as folding and cysteine pairing, addition of complex carbohydrate structures, and secretion of active protein. Vectors useful for the expression of antigen in mammalian cells are characterized by insertion of the antigen coding sequence between a strong viral promoter and a polyadenylation signal. The vectors can contain genes conferring either gentamicin or methotrexate resistance for use as selectable markers. The antigen and immunoreactive fragment coding sequence can be introduced into a Chinese hamster ovary cell line using a methotrexate resistance-encoding vector. Presence of the vector RNA in transformed cells can be confirmed by Northern blot analysis and production of a cDNA or opposite strand RNA corresponding to the antigen coding sequence can be confirmed by Southern and Northern blot analysis, respectively. A number of other suitable host cell lines capable of secreting intact human proteins have been developed in the art, and include the CHO cell lines, HeLa cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc. The vectors containing the nucleic acid segments of interest can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

Alternative vectors for the expression of antigen in mammalian cells, those similar to those developed for the expression of human gamma-interferon, tissue plasminogen activator, clotting Factor VIII, hepatitis B virus surface antigen, protease Nexinl, and eosinophil major basic protein, can be employed. Further, the vector can include CMV promoter sequences and a polyadenylation signal available for expression of inserted nucleic acid in mammalian cells (such as COS7).

The nucleic acid sequences can be expressed in hosts after the sequences have been operably linked to, i.e., positioned, to ensure the functioning of an expression control sequence. These expression vectors are typically replicable in the host organisms either as episomes or as an integral part of the host chromosomal DNA. Commonly, expression vectors can contain selection markers, e.g., tetracycline resistance or hygromycin resistance, to permit detection and/or selection of those cells transformed with the desired nucleic acid sequences (see, e.g., U.S. Pat. No. 4,704,362).

Polynucleotides encoding a variant polypeptide may include sequences that facilitate transcription (expression sequences) and translation of the coding sequences such that the encoded polypeptide product is produced. Construction of such polynucleotides is well known in the art. For example, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

Purified Antibodies

A purified antibody that binds the Black Creek Canal hantavirus or antigenic polypeptides of the present invention, or genetic variants within the Black Creek Canal hantavirus species is also provided. The antibodies can be polyclonal or monoclonal. The antibodies can specifically bind a unique epitope of the virus or a viral antigen. The term "bind" signifies the well understood antigen-antibody interactions or other nonrandom association with an antigen. "Specific binding" as used herein describes an antibody or other ligand that has a higher affinity for its target molecule (e.g., the Black Creek Canal hantavirus species or species-specific antigen) than for non-target molecules (e.g., any virus or viral antigen other than the one specified).

Antibodies can be made by may well-known methods (see also, Harlow and Lane, *Antibodies; A Laboratory Manual*, Cold Spring Harbor Laboratory, Cold Spring Harbor, N.Y., (1988)). Briefly, purified virus or viral antigen can be injected into an animal in an amount and in intervals sufficient to elicit an immune response. Antibodies can either be purified directly, or spleen cells can be obtained from the animal. The cells are then fused with an immortal cell line and screened for antibody secretion. The antibodies can be used to screen nucleic acid clone libraries for cells secreting the antigen. Those positive clones can then be sequenced as described in the Examples or by other methods (see, for example, Kelly et al., *Bio/Technology*, 10:163–167 (1992); Bebbington et al., *Bio/Technology*, 10:169–175 (1992)).

Specific examples of the purified antibody of the invention which specifically binds to Black Creek Canal hantavirus antigens include an antibody which specifically binds to the polypeptide encoded by SEQ ID NO:1 or antigenic fragments thereof. Further examples of the present antibodies include an antibody which specifically binds to the polypeptide encoded by SEQ ID NO:2 or antigenic fragments thereof, and an antibody which specifically binds to the polypeptide encoded by SEQ ID NO:3 or antigenic fragments thereof.

The antibody can be bound to a substrate or labeled with a detectable moiety or both bound and labeled. The detectable moieties contemplated with the composition of the present invention are those listed below in the description of the diagnostic methods, including fluorescent, enzymatic and radioactive markers.

A method of treating hantavirus infection in a subject is also provided. The method comprises administering to a subject a therapeutically effective amount of a purified hantavirus antibody and a pharmaceutically acceptable carrier.

Vaccines

The Black Creek Canal hantavirus or viral antigen, e.g., a purified antigenic polypeptide fragment encoded by the nucleic acids of this invention, can be used in the construction of a vaccine comprising an immunogenic amount of the virus or antigen and a pharmaceutically acceptable carrier. Thus, a live attenuated hantavirus (live vaccine) and a killed virus or viral antigen (killed vaccine) are also provided. The vaccine can be the entire antigen (attenuated or killed virus or antigenic polypeptide), the antigen on the intact new virus, *E. coli* or other strain, or a fragment of an antigen containing an epitope specific to the antigen. The vaccine can be potentially cross-reactive with antibodies to other antigens. The vaccine can then be used in a method of preventing infection with the Black Creek Canal hantavirus described herein. Such Black Creek Canal hantavirus derivatives may be useful in vaccine therapy as a means of conferring immunogenicity to a subject.

"Live vaccines" are attenuated with respect to their ability to cause disease, meaning they are less likely to cause clinical illness than the natural disease-causing agent, but retain the capacity for growth within the host by virtue of their ability to undergo limited replication in the host. Methods of attenuation, include, but are not limited to modification through heating organisms to just below the thermal death point, exposing the organisms to sublethal concentrations of inactivating chemicals, and modification of the viral genome using molecular techniques. Live vaccines can be selected by a number of techniques such as temperature selection and selection for reassortant genomes. Other methods of attenuation involve adapting organisms to grow in atypical conditions, e.g., unnatural hosts, abnormal physiological conditions or a prolonged tissue culture. Prolonged repeated tissue culture of a virus in non-target tissues of the virus derived from the host can result in loss of pathogenicity. These techniques are well known in the art and have resulted in the generation of a number of viable viral vaccines. (See e.g., Sukamaran, M., et al. Exclusive asymptomatic neonatal infections by human rotavirus strains having subgroup I specificity and 'long' RNA electropherotype. Arch. Virol. 126:239–251 (1992) and Roizman, B. and Jenkins, F. J. Genetic engineering of novel genomes of large DNA viruses. Science 229:1208–1214 (1985)). Such vaccines often induce cell mediated (T cell) immunity in addition to antibody mediated (B cell) immunity.

Attenuation of the virus of the present invention may also be achieved by genetic engineering techniques which are known in the art. Given the sequences of the Black Creek Canal hantavirus genome as provided by the invention and set forth in SEQ ID NOS:1–3, one skilled in the art can identify a coding region or gene which is necessary for replication or virulence of the virus and "knock out," delete or render non-sense that portion of the viral genome to inactivate the virus. ("General Principles of Vaccination and Vaccines," Veterinary Immunology, 4th Ed., W. B Saunders Co., 261–276 (1992). (See also, Ada G., The immunological principles of vaccination. Lancet 335:523–526, (1990), Lerner R. A., Synthetic vaccines. Sci Am 248:66–74, (1983), Liew F. Y., New aspects of vaccine development. Clin Exp Immunol 62:225–241, (1985), and Mitchison N. A., Rational design of vaccines. Nature 308:112–113, (1984)).

"Killed" or "non-live" derivatives of the Black Creek Canal hantavirus are also contemplated. In contrast to live vaccines, killed vaccines do not replicate in the host. Consequently, killed vaccines are often less effective in inducing cell mediated immunity and often require the administration of booster inoculations. Killed vaccines, however, cannot revert to a virulent state and are therefore generally safer. Methods of inactivation include, but are not limited to, heat inactivation, chemical inactivation and genetic inactivation and are known in the art. For example, chemical inactivation can include protein denaturation with the use of formaldehyde, alcohol or acetone or alkylating agents such as β-propriolactone or ethelene oxide. There are a number of types of killed vaccines, including killed whole Black Creek Canal hantavirus, purified surface components of the virus, conjugated surface components of the virus, recombinant DNA technology derived proteins from the virus, synthetic peptides of the virus, and anti-idiotype antibodies. Anti-idiotype antibodies are anti-antibodies which have an antigen-combining site that is structurally similar to the original antigen. These anti-idiotypic antibodies can therefore function as a vaccine by inducing an anti-anti-idiotypic antibody which is similar to the first antibody. An anti-idiotype vaccine utilizing a second monoclonal antibody directed against the idiotype of a first monoclonal antibody whose binding site is an epitope on the Black Creek Canal hantavirus is specifically contemplated. This approach has been applied in formulating a vaccine for hepatitis B. (Kennedy, R. C., et al., Anti-idiotypic antibody vaccine for type B viral hepatitis in chimpanzees. Science 232:220–223 (1986)).

It is also specifically contemplated that the vaccines of the present invention can be made utilizing recombinant techniques known in the art. Viral nucleic acid coding for an antigenic peptide can be isolated and inserted into a suitable expression vector, e.g., a Baculovirus, Adenovirus, yeast, *E. coli* or other vector described herein or known in the art. For example, the S segment RNA encoding the nucleocapsid protein or M segment RNA encoding surface glycoproteins G1 and G2 as provided by the invention can be reverse transcribed into cDNA. The cDNA encoding the antigenic peptide can then be isolated by restriction endonuclease digestion and inserted into a suitable vector, e.g., *E. coli*, and expressed. The expressed protein can be purified and combined with a suitable adjuvant for use as a vaccine. Alternatively, the gene of interest can be inserted into an attenuated living carrier organism for direct injection into the host. The commonly preferred technique is the use of recombinant DNA methodology to isolate, clone, and express a part of the virulent virus in an expression vector, which in itself can confer immunity to the subject. For example, the surface antigen from Hepatitis B virus has been cloned into an expression vector and the protein produced by that construct is morphologically and immunologically similar to plasma-derived hepatitis B surface antigen. (Scolnick, E. M., et al., Clinical evaluation in healthy adults of a hepatitis B vaccine made by recombinant DNA. J. A. M. A. 251:2812–2814 (1984)).

The antigenic polypeptides of the Black Creek Canal hantavirus can also be synthesized by utilizing an epitope of the virus which confers protective immunity, e.g., a capsid protein. Suitable epitopes can be predicted utilizing the nucleic acid sequences of the invention in conjunction with computer-generated models of the protein and monoclonal antibodies to identify critical protective components. Techniques for synthesis of such peptides are known in the art.

Active immunization can be achieved through natural infection with an organism or virus, or artificially by vaccination. (Kuby, J. Immunology, W. H. Freeman and Co., New York (1992)). Specifically, this artificial immunization can occur by vaccination of a subject with attenuated viruses, with inactivated viruses, with purified viral macromolecules, with recombinant antigens derived from viral antigens, with multivalent subunit vaccines, or anti-idiotype vaccines.

It is also contemplated that immunization against disease caused by a Black Creek Canal hantavirus can be achieved by a "naked" DNA vaccine approach. Briefly, DNA constructs containing promoter sequences upstream of Black Creek Canal hantavirus antigen coding sequences can be injected into muscle tissue or administered via the mucosa and result in expression of viral antigens that induce a protective immune response.

Immunogenic amounts of the vaccine antigen can be determined using standard procedures. Briefly, various concentrations of a putative specific immunoreactive epitope are prepared, administered to a subject and the immunological response (e.g., the production of antibodies or cell mediated immunity) of the subject to each concentration is determined.

Accordingly, therefore, the present invention provides a vaccine comprising the Black Creek Canal hantavirus (attenuated or killed), an immunogenic polypeptide or fragments of the polypeptides. Examples of such polypeptides include those derived from a purified polypeptide encoded by the nucleotide sequences set forth in the Sequence Listing as SEQ ID NO:1, SEQ ID NO:2 or SEQ ID NO:3. Such a vaccine would naturally include immunogenic amounts of the virus or polypeptide fragments and a pharmaceutically acceptable carrier.

The pharmaceutically acceptable carrier contemplated herein can comprise saline or other suitable carriers (Arnon, R. (Ed.) *Synthetic Vaccines* I:83–92, CRC Press, Inc., Boca Raton, Fla., (1987)). By "pharmaceutically acceptable" is meant a material that is not biologically or otherwise undesirable, i.e., the material may be administered to an individual along with a selected compound without causing any undesirable biological effects or interacting in a deleterious manner with any of the other components of the pharmaceutical composition in which it is contained. The carrier will depend upon the method of administration and choice of adjuvant if one is used. An adjuvant can also be a part of the carrier of the vaccine, in which case it can be selected by standard criteria based on the antigen used, the mode of administration and the subject (Arnon, R. (Ed.), 1987). Methods of administration can be by oral or sublingual means, or by injection, depending on the particular vaccine used and the subject to whom it is administered.

It can be appreciated from the above that the vaccine can be used as a prophylactic or a therapeutic modality. Thus, the invention contemplates methods of preventing or treating infection from the Black Creek Canal hantavirus and the associated diseases by administering the vaccine to a subject.

EXAMPLE 1

ISOLATION OF BLACK CREEK CANAL VIRUS, A NEW HANTAVIRUS FROM *SIGMODON HISPIDUS* IN FLORIDA

Trapping and Processing of Rodents: In January and February 1994, rodents were trapped on 2 different occasions at selected sites in the grassy fields around (10–15 miles radius), the semi-rural residence of the HPS case. Live-trapping was conducted using standardized protocols (Childs J. E., et al., Serologic and genetic identification of *Peromyscus maniculatus* as the primary rodent reservoir for a new hantavirus in the southwestern United States. Journal of Infectious Diseases 169:1271–1280 (1994)). Special precautions for handling potentially infected rodents were taken (i.e., full-face respirators equipped with HEPA filters, disposable gowns, gloves, and shoe covers). The live-captured rodents were anesthetized, identified by species, and then bled and euthanized. Sera and carcasses were stored in dry ice and shipped to the Centers for Diseases Control and Prevention (CDC), where lungs, liver, spleen, kidneys were removed aseptically and stored at −70° C.

Safety and Handling of Samples: Due to the suspected hazardous nature of the agent, all steps of the homogenization of rodent tissue samples, cell inoculation, and the RNA extraction and purification were performed in a certified laminar flow biocontainment hood within a Biosafety Level (BSL) 3 containment laboratory (Centers for Disease Control. Laboratory management of agents associated with Hantavirus pulmonary syndrome: Interim biosafety guidelines. Morbidity and Mortality Weekly Report 43, RR1-7 (1994)) where no known hantaviruses were handled.

Enzyme-Linked Immunosorbent Assay (ELISA): The IgG ELISA was performed as previously described (Elliott L., et al., Isolation of the causative agent of hantavirus pulmonary syndrome. American Journal of Tropical Medicine and Hygiene 51:102–108 (1994)), by coating the plate directly with a basic buffer detergent extract of cells infected with SEO (prototype: 80-39), PH (PH-1), and the Sigmodon-derived hantaviruses or uninfected Vero E6 cells. An *Escherichia coli* recombinant SN nucleocapsid antigen was used in the same ELISA format, accompanied by an appropriate negative control antigen (Feldmann H., et al., Utilization of autopsy tissue RNA for the synthesis of the nucleocapsid antigen of a newly recognized virus associated with hantavirus pulmonary syndrome. Virus Research 30:351–367 (1993)). Whole blood specimens were initially diluted 1:100, followed by fourfold dilutions through 1:6400, in 5% skim milk in phosphate-buffered saline (PBS) -TWEEN® 20 (polyoxyethylenesorbitan monolaurate) (SM-PBS-TW) and allowed to react with the antigen-coated wells. Bound IgG was detected with a mixture of goat anti-rat and goat anti-Peromyscus IgG conjugated to horseradish peroxidase (K&P, Gaithersburg, Md.). Optical densities at 410 nm ($OD_{410}$) were recorded on a microplate spectro-photometer and the $OD_{410}$ of the uninfected, antigen-coated well was subtracted from its corresponding virus antigen-coated well to yield the adjusted $OD_{410}$.

Immunofluorescent Assay (IFA): Slides with cells scraped from inoculated flasks were air-dried and gamma-irradiated ($1\times10^6$ rads) and fixed in acetone as previously described. (Johnson K. M., et al., Preparation of polyvalent viral immunofluorescent intracellular antigens and use in human serosurveys. Journal of Clinical Microbiology 14:527–529 (1981)). Hantavirus antigen was detected by IFA using HPS convalescent-phase human serum (#9302207) and mouse monoclonal (GB04-BF07) antibody with a broad reactivity against all known hantaviruses, and specific anti-species FITC conjugates.

Reverse-Transcriptase PCR (RT-PCR): Rodent lung samples and passaged Vero E6 cells infected with the Sigmodon-derived hantavirus were analyzed using a nested RT-PCR assay after RNA extraction, as previously described (Nichol, S. T., et al., Genetic identification of a hantavirus associated with an outbreak of acute respiratory illness. Science 262:914–917 (1993) and Spiropoulou et al., Genome structure and variability of a virus causing hantavirus pulmonary syndrome. Virology 200:715–723.(1994)). Specific nested PCR DNA products were extracted from agarose gels, and di-deoxynucleotide cycle sequence analysis was carried out (Applied BioSystems, Foster City, Calif., and Nichol et al., (1993)).

Phylogenetic Analysis: Phylogenetic analysis of nucleotide sequence differences between previously characterized hantaviruses and PCR fragments generated from hantaviruses detected in infected Sigmodon lung tissues or infected cell culture material were analyzed by the maximum parsimony method using PAUP software (Swofford, D. L. PAUP: Phylogenetic Analysis Using Parsimony, Version 3.0s. Computer program. Illinois Natural History Survey, Champaign, Ill. (1991)). Analysis was carried out by a branch and bound search, using a weighing of transversions over transitions of 4:1. This weighing was based on prior MacClade software analysis (Maddison, W. P.,et al., MacClade: Analysis of phylogeny and character evolution. Sunderland, MA: Sinauer (1992)) of trees generated from nucleotide sequence differences detected among numerous SN virus variants which estimated transition : transversion ratios of 4.6:1 (Spiropoulou et al., 1994). Such weighing is predicted to improve the effectiveness of the maximum parsimony method for estimation of the correct phylogeny. (Hillis, D. M., et al., Application and accuracy of molecular phylogenies. Science 264,671–677 (1994)). Bootstrap confidence limits were calculated by 1000 repetitions of the analysis. Previously published hantavirus sequences were included in the analysis: HTN strains 76–118 [GenBank M14627 and X61034], Lee [GenBank D00377], and HV-114 [GenBank L08753]; Seoul strains 80–39 [GenBank S47716], SR-11 [GenBank M34882], and Thai [GenBank L08756]; PUU strains Sotkamo [GenBank X61034], CG18-20 [GenBank M29979], and Berkel (*Pilaski* et al., Genetic identification of a new Puumala virus strain causing severe hemorrhagic fever with renal syndrome in Germany. Journal of Infectious Diseases (in press) (1994)); PH strain PHV-1 [GenBank X55129] and SN viruses CA H19 and NM H10 (Nichol et al., (1993); Spiropoulou et al., (1994)).

Virus Isolation: The HUVEC (endothelial) cell line and Vero E6 cell line (ATCC Vero clone CRL 1586) were grown in Eagle's minimum essential medium (EMEM) supplemented with 10% heat-inactivated fetal bovine serum (FBS) and antibiotics. After inoculation and adsorption of inoculum, growth medium was replaced with maintenance medium (2% FBS). Cell cultures in T-25 flasks were inoculated with 0.1 ml of a 10% tissue (lung and spleen) suspension, maintained at 37° C. with medium changed every 7 days, and blind passed at intervals of 2 weeks. At the time of passage, the supernatant was poured into a conical centrifuge tube, and the remaining cells were trypsinized and then mixed with the supernatant. One-third of this mixture was passed into fresh cultures and one-third was frozen; the cells in the remaining third were gently pelleted and mixed with 0.2 ml of saline, and slides were prepared for the IFA.

Characterization of the Sigmodon-derived Hantavirus Isolate: The hantavirus isolated from Sigmodon was compared with HTN, PUU, SEO, PH, and SN hantaviruses by cross-IFA and cross-ELISA, using HTN-, PUU-, SEO-, PH-and, SN-serotype specific antisera from immune rabbits, and serum from the wild-caught *S. hispidus* from which the hantavirus was isolated. All sera were serially diluted in SM-PBS-TW, twofold starting from 1:16 for the IFA and fourfold starting from 1:100 for the ELISA.

Rodent Capture and Serology: Sigmodon hispidus was the most abundant rodent captured (90/199; 45.2%) (Table 1). In the ELISA IgG test, the seropositivity in this species varied between 2.2% (SEO antigen) and 16.7% (SN antigen) and was 17.7% with the Sigmodon isolate antigen. Most of the animals positive with the Sigmodon hantavirus isolate were cotton rats (16/19, 84.2%), although two Norway rats (*R. norvegicus*) and one rice rat (*Oryzomys palustris*) were also found to be positive (Table 1).

Isolation: Isolation attempts were initiated on seven ELISA antibody-positive Sigmodon tissues. Lung and spleen homogenates from 7 of the 16 serologically confirmed Sigmodon were inoculated on Vero E6 and HUVEC cell lines. Hantavirus isolation was unsuccessful using the HUVEC cell line. However, intra-cytoplasmic hantavirus inclusions were detected by IFA in Vero E6 cells after passage of cultures initiated with homogenates from cotton rats 9408082 and 9408076. These cultures showed 5% and 20% fluorescent cells after one passage, and 25% and 90–100% fluorescent cells after two passages, respectively. On subsequent passages, a cytopathogenic effect could be detected in hantavirus-infected Vero E6 cells on days 8–10 postinfection.

RT-PCR: RNA extraction and RT-PCR analysis were performed on lung tissues from thirteen of the ELISA-seropositive Sigmodon. A positive DNA product band of the correct approximate size (139 nucleotides) was obtained for each rodent but was absent in the negative controls. The nucleotide sequence of the PCR band amplified from lung RNA of rodent #9408076 was determined directly and found to be different from the previously characterized hantaviruses, including the newly described SN hantavirus (Nichol et al., 1993; Spiropoulou et al., 1994). Phylogenetic analysis of the nucleotide sequence differences by the maximum parsimony method using PAUP software (Swofford, 1991) confirmed that the Sigmodon-derived hantavirus unique and represented a newly recognized hantavirus lineage (FIG. 1). The PCR band and virus nucleotide sequence obtained from the virus present in the third Vero E6 passage (#807040) of original lung suspension were identical to those obtained originally from the rodent tissues (lungs #9408076) from which the isolate was made.

Antigenic Characterization of the Sigmodon Hantavirus Isolate: The hantavirus (807040) obtained from Sigmodon lung 9408076 was characterized by cross-IFA and cross-ELISA. By cross-IFA, the Sigmodon-derived isolate was readily discernible from the HTN, SEO, and PH hantaviruses but showed a two-way antigenic cross-reactivity with SN and PUU hantaviruses (Table 2). The ELISA results demonstrated that the Sigmodon hantavirus isolate is antigenically distinct from the other hantaviruses on the basis of the ability of the Sigmodon immune serum to recognize only the homologous preparation (Table 3). In addition, the Sigmodon hantavirus antigen could be differentiated from those of all previously known hantavirus serotypes by using monoclonal antibodies.

During the epidemiologic investigation, several species of rodents were trapped from various locations in Dade county, Fla., where the HPS patient had resided. This area is outside the normal geographic range of the deer mice (*P. maniculatus*) and none were trapped. Cotton rats (*S. hispidus*) represented nearly half of all rodents trapped and virtually all of the seropositive rodents. Hantavirus antibody prevalence in cotton rats was 17.8% using the Sigmodon-isolate antigen. Hantaviruses have historically been difficult to isolate from human or rodent specimens, leading to a delay of several years. (Lee, H. W., et al., Isolation of the etiologic agent of Korean hemorrhagic fever. Journal of Infectious Diseases 137:298–308 (1978) French, G. R. et al., Korean hemorrhagic fever: propagation of the etiologic agent in a cell line of human origin. Science 211:1046–1048 (1981) ; Niklasson, B. et al., Isolation of the nephropathia epidemica agent in Sweden. Lancet i:1012–1013 (1984); Yanagihara et al., Propagation of nephropathia epidemica in cell culture. Lancet i:1013 (1984)) or months (Elliott et al., 1994) between the clinical description of disease in humans and the cell culture propagation of the etiologic agent. In this case, we clearly demonstrate, for the first time, the successful isolation and propagation in Vero E6 cells of a hantavirus from wild-caught *S. hispidus*. Classic antigen inclusion bodies were demonstrated by IFA in infected cell culture after the first passage.

Cross-IFA and cross-ELISA data confirm the results of previous serologic studies that indicate a close relationship between HTN and SEO hantaviruses and a most distant relationship between PUU and PH hantaviruses. (Chu, Y. K. et al., Serological relationships among viruses in the Hantavirus genus, family Bunyaviridae. Virology 198: 196–204 (1994).) Sequence information obtained by RT-PCR directly from the original cotton rat tissues or from the cell culture-passaged material demonstrated a close relationship of this hantavirus with SN hantavirus, but clearly placed this hantavirus in a new lineage.

The Vero E6-propagated virus was used to make diagnostic reagents for ELISA IgM and IgG. Rodent seroprevalence was higher using this homologous antigen than the SN hantavirus antigen. In the IgM capture ELISA format, IgM could be demonstrated in the Florida HPS patient only with this Sigmodon hantavirus antigen. We refer to this virus species as Black Creek Canal hantavirus after a geographic landmark near the *S. hispidus* capture site.

TABLE 1

Rodent captures and serologic results

| SPECIES | No. submitted | SEO ELISA IgG | PH ELISA IgG | SN ELISA IgG | Sigmodon virus isolate ELISA IgG |
|---|---|---|---|---|---|
| *Mus musculus* (house mouse) | 75 | 0(0%) | 0(0%) | 0(0%) | 0(0%) |
| *Sigmodon hispidus* (cotton rat) | 90 | 2 (2.2%) | 7 (7.8%) | 15 (16.7%) | 16 (17.8%) |
| *Rattus noivegicus* (brown or norway rat) | 7 | 0(0%) | 0(0%) | 0(0%) | 2(1%) |
| Rattus(black or roof rat) | 7 | 0(0%) | 0(0%) | 0(0%) | 0(0%) |
| Rattus sp. | 2 | 0(0%) | 0(0%) | 0(0%) | 0(0%) |
| *Oryzomys palustris* (rice rat) | 18 | 0(0%) | 0(0%) | 1(5.5%) | 1(5.5%) |
| TOTAL | 199 | 2(1%) | 7(3%) | 16(8%) | 19 (9.5%) |

(SEO = Seoul; PH = Prospect Hill; SN = Sin Nombre)

TABLE 2

Cross-IFA characterization of the
Sigmodon-derived virus isolate (807040)

| Antiserum | Antigens | | | | | |
|---|---|---|---|---|---|---|
| m | HTN | SEO | PUU | SN | 807040 | PH |
| HTN | 2048 | 1024 | 128 | 128 | 128 | 64 |
| SEO | 2048 | 8192 | 128 | 512 | 2048 | 128 |
| PUU | 32* | 128 | 2048 | 512 | 256 | 1024 |
| SN | 256 | 256 | 1024 | 8192 | 4096 | 1024 |
| Sigmodon immune serum | 256 | 512 | 512 | 1024 | 4096 | 256 |
| PH | 32* | 32* | 256 | 256 | 256 | 512 |

(HTN = Hantaan; SEO = Seoul; PUU = Puumala; SN = Sin Nombre; PH = Prospect Hill;
*= nonspecific staining due to the presence of anti-Vero cell antibodies)

TABLE 3

Cross-ELISA characterization of the
Sigmodon-derived virus isolate (807040)

| Antiserum | Antigens | | | | | |
|---|---|---|---|---|---|---|
| | HTN | SEO | PUU | SN | PH | 807040 |
| HTN | 25,600 | 1,600 | 400 | 100 | 400 | 1,600 |
| SEO | 25,600 | 25,600 | 6,400 | 1,600 | 1,600 | 6,400 |
| PUU | 25 | 25 | 1,638,400 | 25,600 | 25,600 | 102,400 |
| SN | 1,600 | 400 | 25,600 | 25,600 | 25,600 | 102,400 |
| PH | 25 | 25 | 1,600 | 6,400 | 25,600 | 25,640 |
| Sigmodon immune serum | 25 | 25 | 25 | 25 | 25 | 6,400 |

(HTN = Hantaan; SEO = Seoul; PUU = Puumala; SN = Sin Nombre; PH = Prospect Hill)

EXAMPLE 2

ISOLATION AND PARTIAL CHARACTERIZATION OF A HANTAVIRUS FROM A LIVING HUMAN

We report the first isolation of hantavirus in France and Western Europe from a case of nephropathia epidemica (NE) acquired in France. This hantavirus was isolated directly from a serum collected in the acute phase of the clinical course, by successive blind passages in Vero E-6 cells rather than first passing the hantavirus through laboratory rodents. This technique is applicable to all species of hantaviruses. Serologic typing using monoclonal antibodies confirmed the identity of the virus as Puumala (PUU). The sequence of an 832 nucleotide fragment of the virus M segment obtained by PCR also classified it as a PUU hantavirus.

A 20-year-old French recruit was admitted to a military hospital (H.I.A. Desgenettes, Lyon), for suspected meningitis with a 4-day history of high fever (40° C.), myalgia, posterior and frontal headaches, photophobia, and vomiting. Facial flush and petechiae on the soft palate were noted on admission. Spinal fluid showed no abnormalities. Over the following days, the fever persisted despite treatment with antipyretics. The patient developed epistaxis, lumboabdominal pains, and oliguria. Two days later his condition deteriorated with signs of acute renal failure: elevated creatinine (266 $\mu$mol/L), proteinuria (1.7 g/L), microscopic hematuria (dipstick test) with a urine volume of 800 ml/24 h. Liver enzymes were within the normal range. Acute hemorrhagic fever with renal syndrome (HFRS) was serologically confirmed.

Virus isolation was performed by seeding a serum sample (day 6 post-onset) on a monolayer of Vero E-6 cells, followed by incubation at 37° C. for 14 days. Passage of cells was continued approximately every 14 days. Virus antigen was detected by an immunofluorescence test in 10–15% of cells at the third passage and 50–60% of cells at the fourth passage, 45 and 60 days post-inoculation, respectively. No cytopathic effect was observed. Serologic typing using a panel of monoclonal antibodies (kindly provided by J. W. LeDuc, US Army Medical Research Institute of Infectious Diseases, Frederick, Md.) and phylogenic analysis (Phylogenetic Analysis Using Parsimony (PAUP)) of an 832 nucleotide region from the virus M segment identified the newly isolated virus (PUU90-13) as belonging to the Puumala serotype.

Virus isolation attempts using sera collected during the later renal phase of HFRS and NE are generally unsuccessful. In this instance, the serum used for the successful virus isolation was collected on the day of admission and had been kept frozen (−70° C.) until virus isolation was attempted.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

What is claimed is:

1. A method of detecting a current or previous infection by Black Creek Canal hantavirus in a subject comprising the steps of:
   (a) contacting an antibody-containing sample from the subject with an antigen which is specific to Black Creek Canal hantavirus; and
   (b) detecting any binding of said antibody with said antigen, wherein binding of said antibody with said antigen indicates a current or previous infection with Black Creek Canal hantavirus, wherein said antigen is the polypeptide encoded by the nucleotide sequence set forth in the Sequence Listing as SEQ ID NO: 1, the polypeptide encoded by the nucleotide sequence set forth in the Sequence Listing as SEQ ID NO:2, or the polypeptide encoded by the nucleotide sequence set forth in the Sequence Listing as SEQ ID NO:3.

2. The method of claim 1, wherein said antigen is the polypeptide encoded by the nucleotide sequence set forth in the Sequence Listing as SEQ ID NO: 1.

3. The method of claim 1, wherein said antigen is the polypeptide encoded by the nucleotide sequence set forth in the Sequence Listing as SEQ ID NO:2.

4. The method of claim 1, wherein said antigen is the polypeptide encoded by the nucleotide sequence set forth in the Sequence Listing as SEQ ID NO:3.

* * * * *